(12) United States Patent
Downie et al.

(10) Patent No.: US 10,064,574 B2
(45) Date of Patent: Sep. 4, 2018

(54) USE OF AUTOMATIC FLOW REGULATORS FOR FLOW MODULATION DURING BLOOD COLLECTION

(71) Applicant: Becton, Dickinson and Company, Franklin Lakes, NJ (US)

(72) Inventors: Patrick Downie, Apex, NC (US); Jamieson W. Crawford, Cliffside Park, NJ (US); Craig Owen Russ, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 453 days.

(21) Appl. No.: 13/737,160

(22) Filed: Jan. 9, 2013

(65) Prior Publication Data

US 2013/0178760 A1  Jul. 11, 2013

Related U.S. Application Data

(60) Provisional application No. 61/584,451, filed on Jan. 9, 2012.

(51) Int. Cl.
| | |
|---|---|
| *A61B 5/15* | (2006.01) |
| *A61M 39/24* | (2006.01) |
| *A61B 5/153* | (2006.01) |
| *A61B 5/154* | (2006.01) |
| *A61M 39/06* | (2006.01) |

(52) U.S. Cl.
CPC ........ *A61B 5/150946* (2013.01); *A61B 5/153* (2013.01); *A61B 5/15003* (2013.01); *A61B 5/154* (2013.01); *A61B 5/150221* (2013.01); *A61B 5/150732* (2013.01); *A61M 39/24* (2013.01); *A61M 2039/0666* (2013.01); *A61M 2039/244* (2013.01); *A61M 2039/246* (2013.01); *A61M 2039/2433* (2013.01); *Y10T 137/7847* (2015.04)

(58) Field of Classification Search
CPC ........ A61B 5/150221; A61B 5/150213; A61B 5/150732; A61B 5/150946; A61B 5/150519; A61B 5/153; A61B 5/154; A61B 5/1438; A61M 5/16877; A61M 5/16881; A61M 39/24; A61M 2039/027; A61M 2039/0666; A61M 2039/2433; A61M 2039/244; A61M 2039/246
USPC ................... 137/513.3, 527–527.8, 843–860
See application file for complete search history.

(56) References Cited

U.S. PATENT DOCUMENTS

| | | | |
|---|---|---|---|
| 2,877,792 A * | 3/1959 | Tybus | F16K 15/038 137/512.1 |
| 3,169,548 A * | 2/1965 | McIntosh | F16K 24/04 137/513.3 |

(Continued)

*Primary Examiner* — David J McCrosky
(74) *Attorney, Agent, or Firm* — The Webb Law Firm

(57) ABSTRACT

A flow regulator for a blood collection assembly includes a housing having an inlet and an outlet, which defines an interior space between the inlet and the outlet. A membrane having a first surface and a second surface is disposed at least partially within the interior space. The membrane has a first position where a flow path between the inlet and the outlet is substantially open, and a second position where the flow path between the inlet and the outlet is at least partially restricted. The membrane is configured to move between the first and second positions in response to a pressure differential acting on the membrane.

5 Claims, 22 Drawing Sheets

(56) References Cited

U.S. PATENT DOCUMENTS

| | | | | |
|---|---|---|---|---|
| 3,848,579 A | * | 11/1974 | Villa-Real | 600/577 |
| 4,244,379 A | * | 1/1981 | Smith | A61B 5/15003 |
| | | | | 600/579 |
| 5,004,010 A | * | 4/1991 | Huet | F16K 17/28 |
| | | | | 137/513.3 |
| 5,406,976 A | * | 4/1995 | Bekki | F16H 61/0009 |
| | | | | 137/513.3 |
| 6,102,680 A | * | 8/2000 | Fraser | F16K 15/16 |
| | | | | 137/246 |
| 8,002,040 B2 | * | 8/2011 | May | E21B 34/10 |
| | | | | 137/513.3 |

* cited by examiner

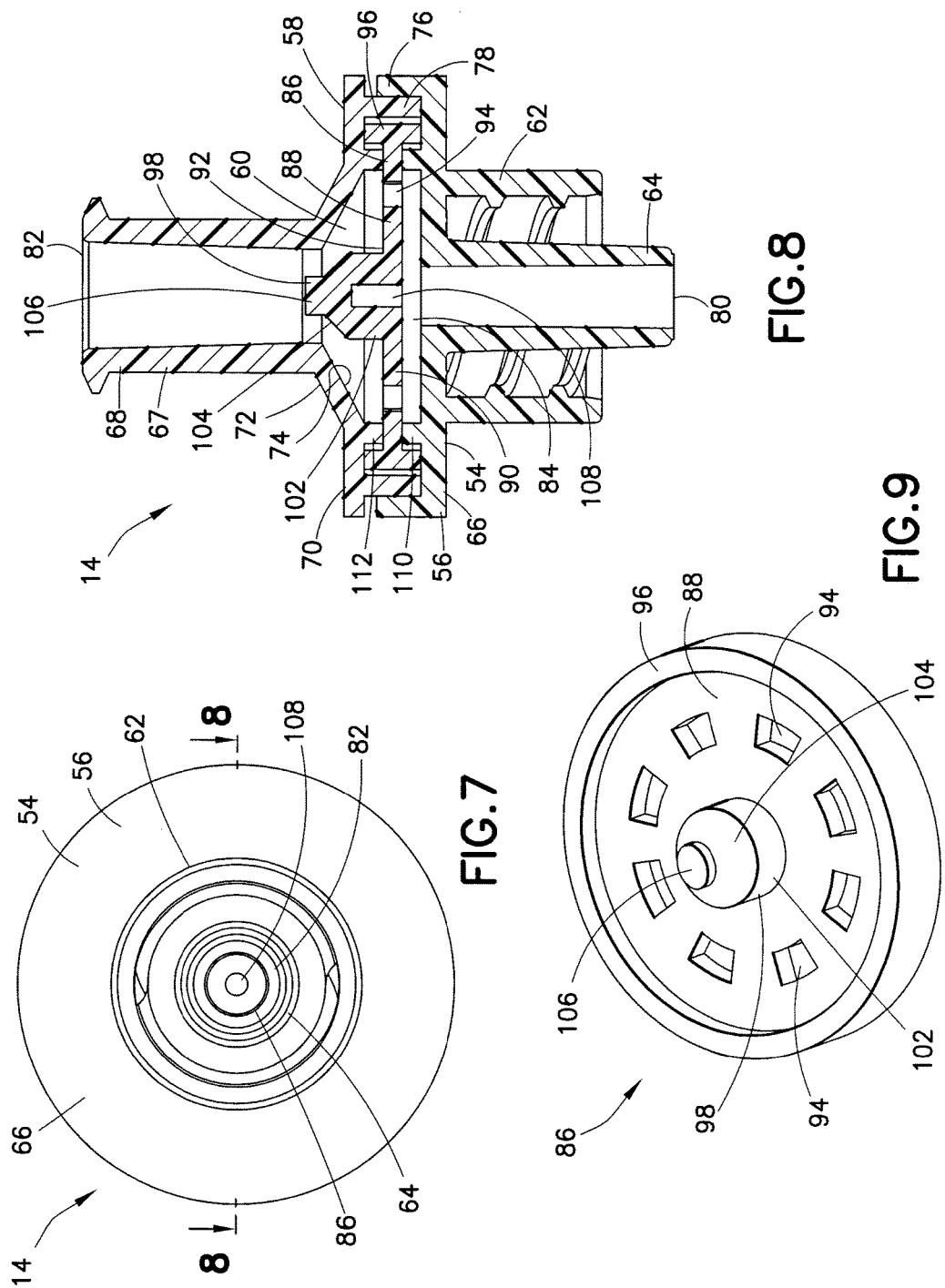

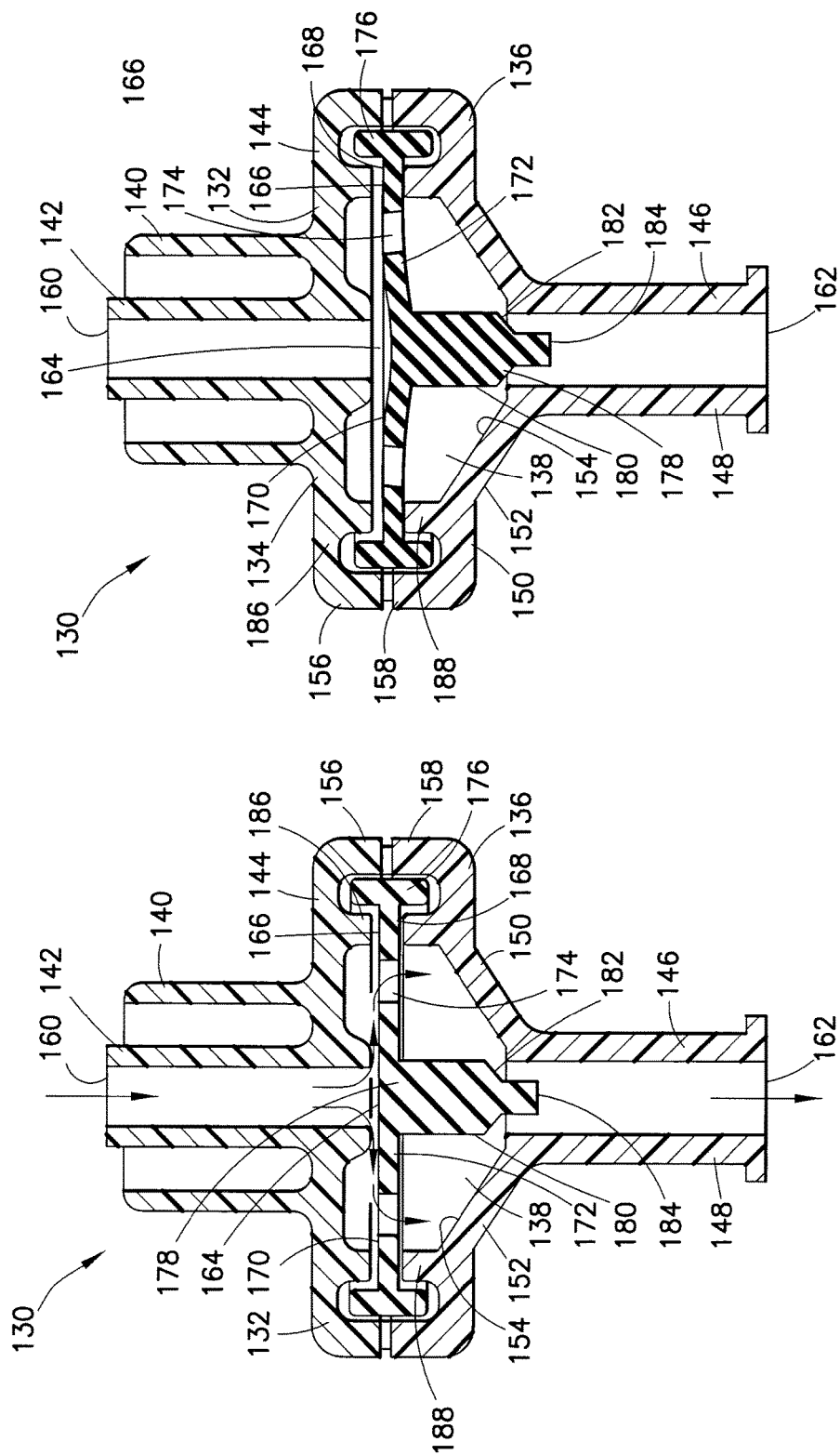

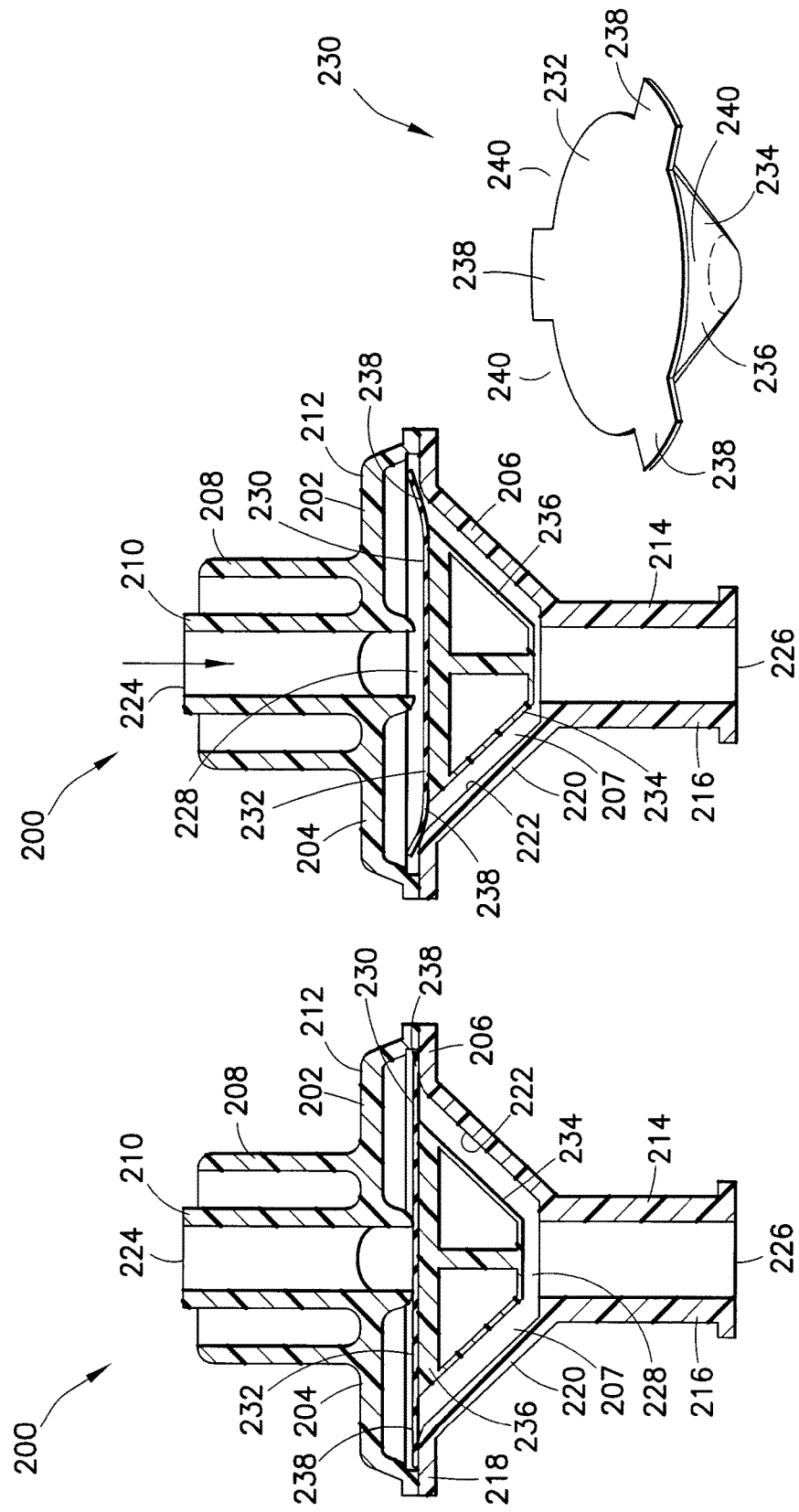

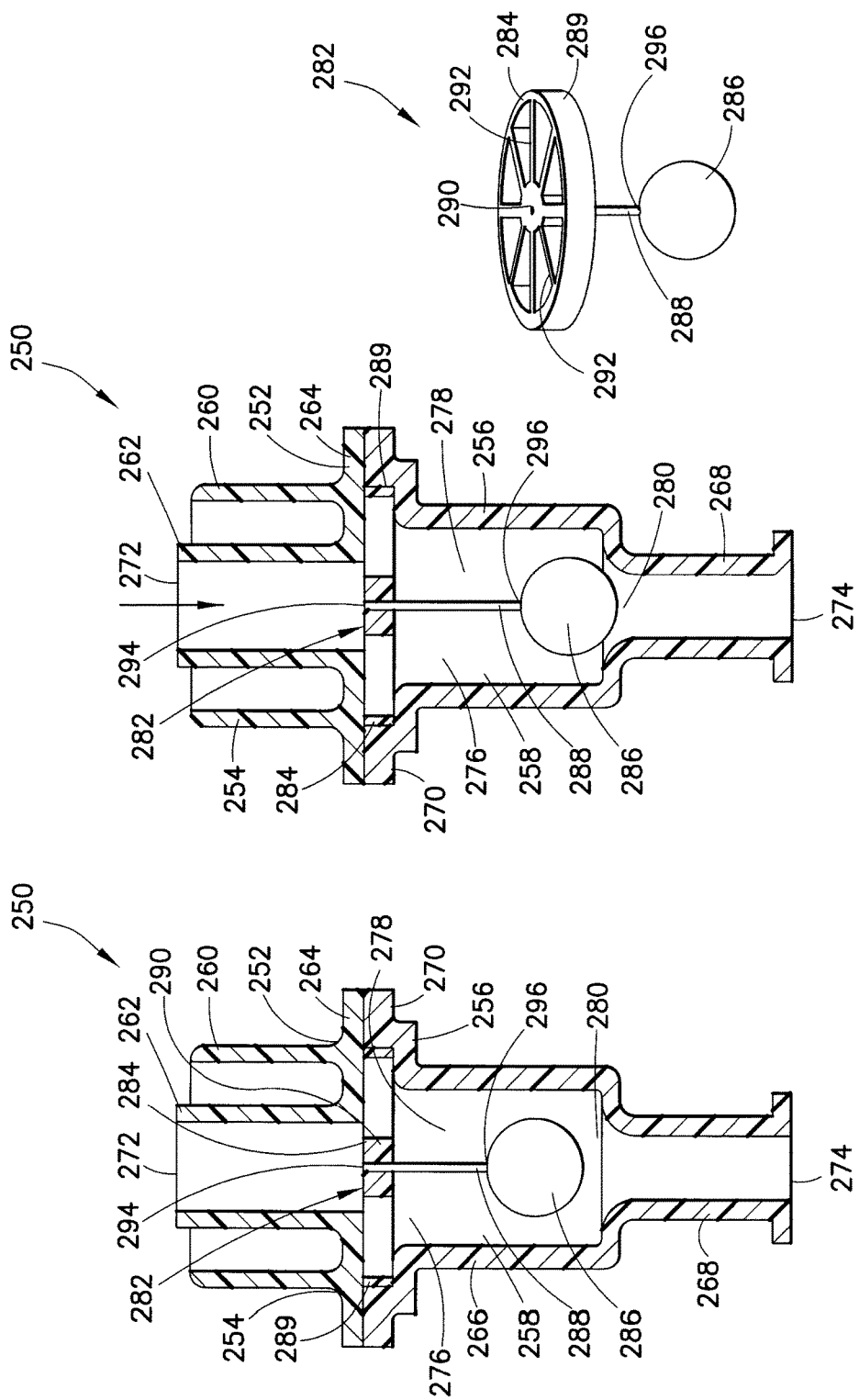

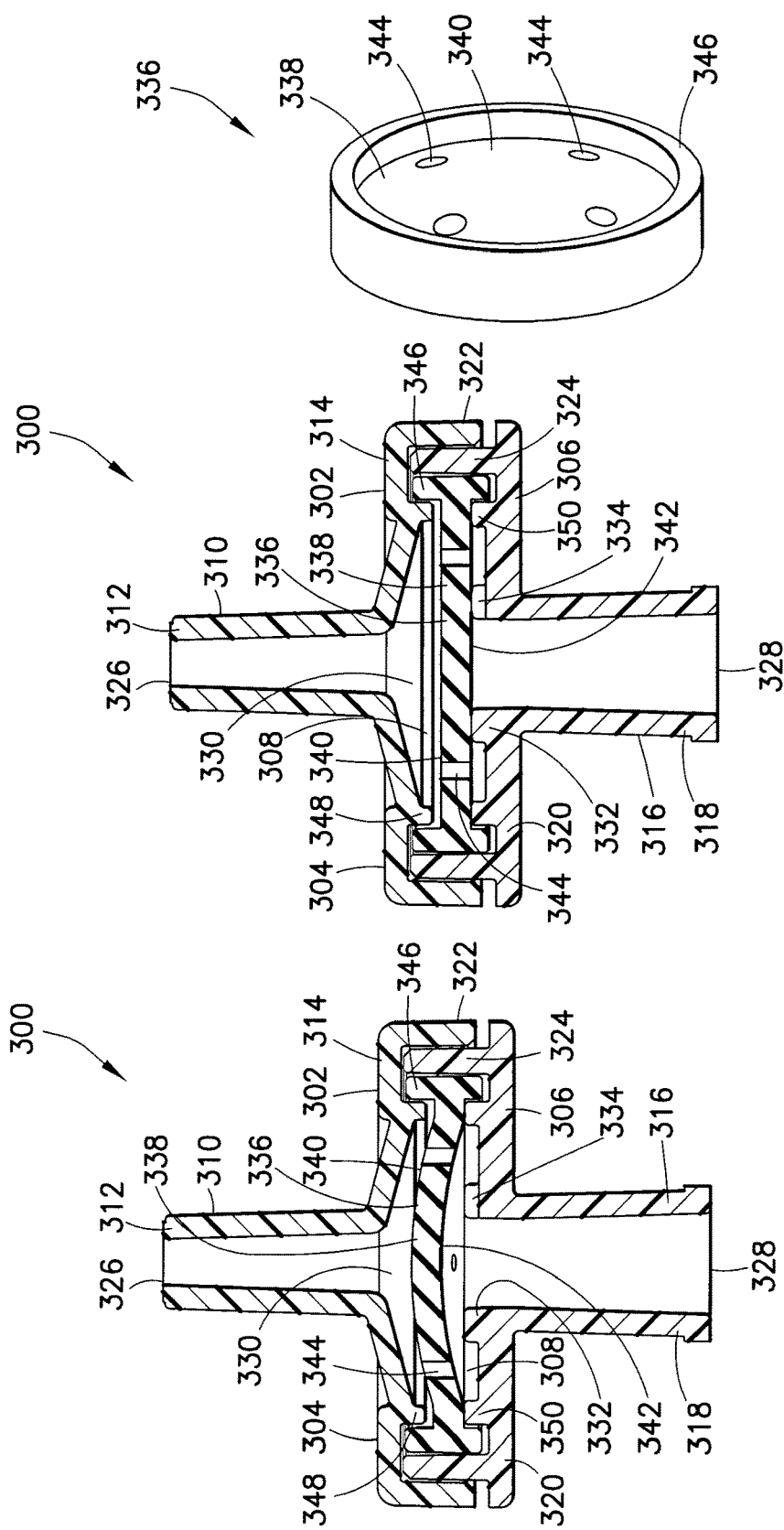

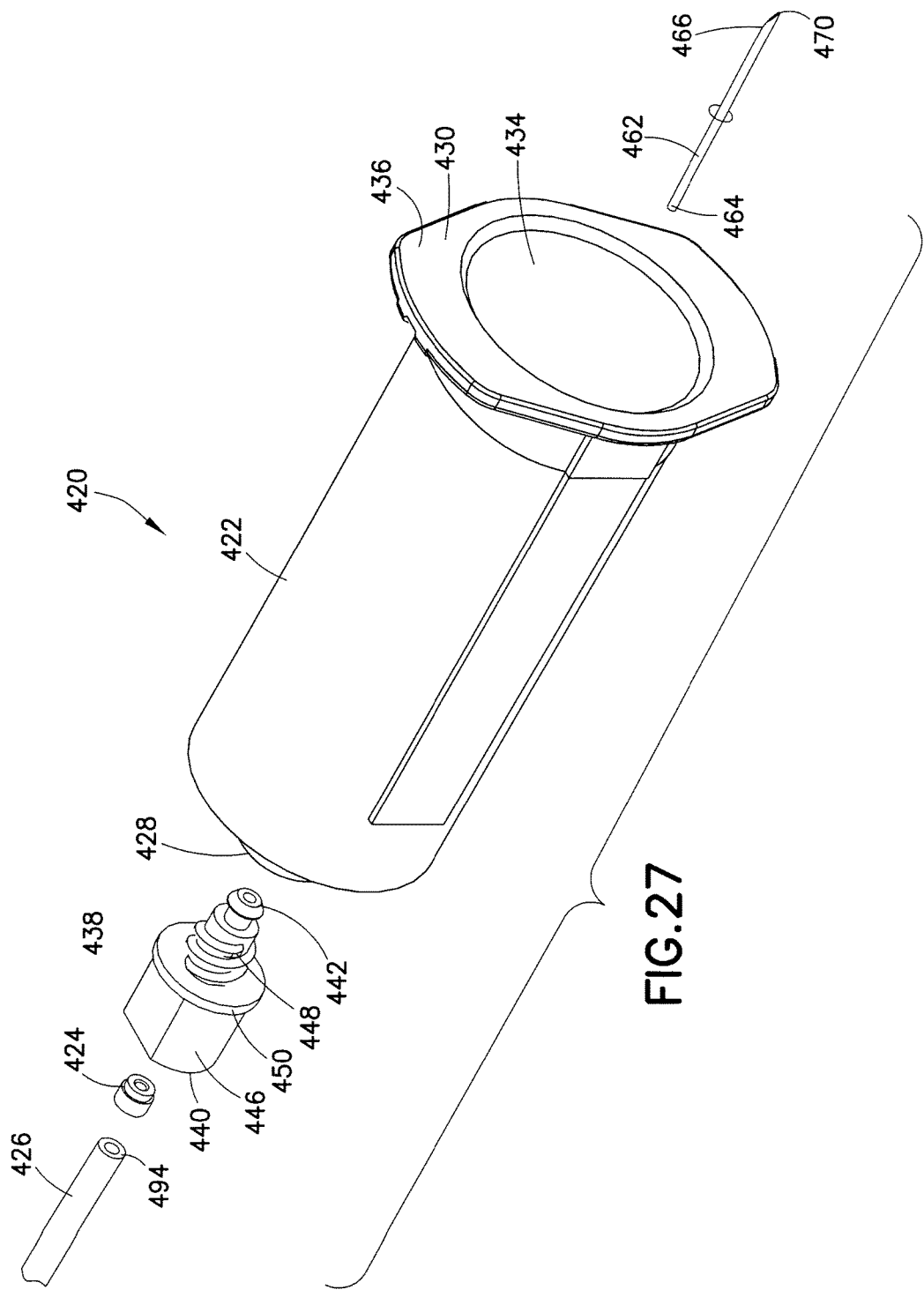

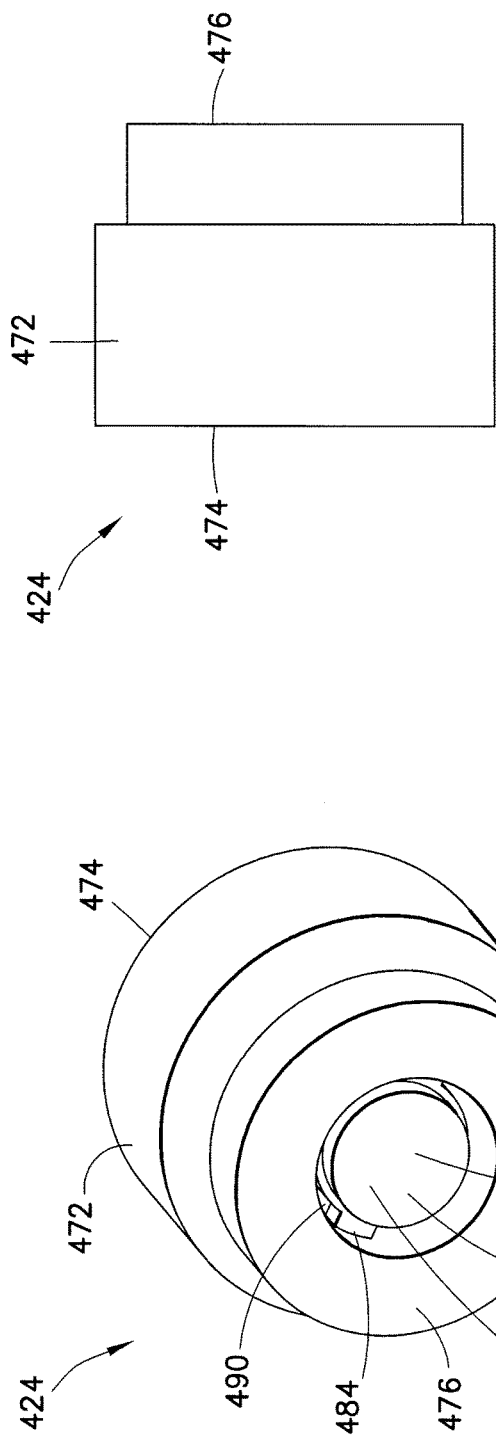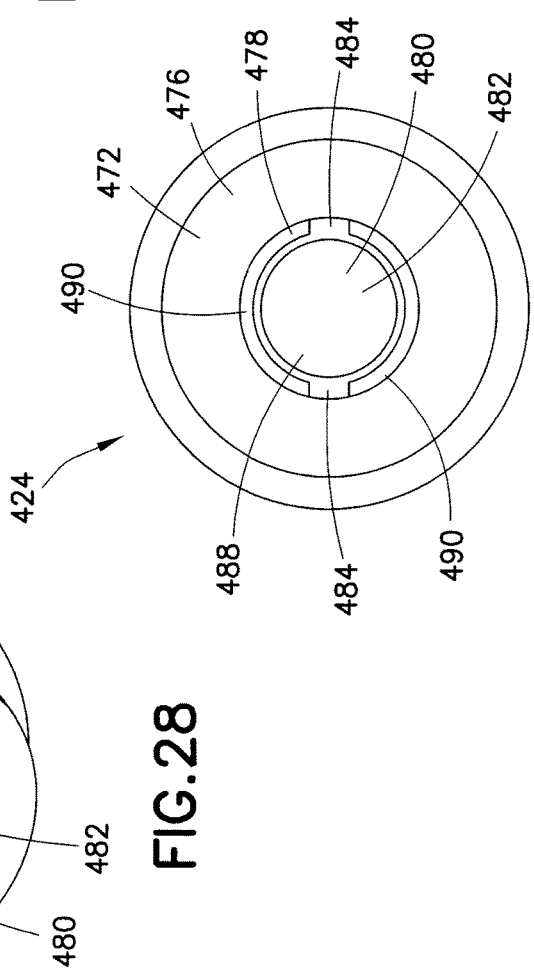

USE OF AUTOMATIC FLOW REGULATORS FOR FLOW MODULATION DURING BLOOD COLLECTION

CROSS-REFERENCE TO RELATED APPLICATION

The present application claims priority to U.S. Provisional Patent Application No. 61/584,451 filed Jan. 9, 2012, entitled "Use of Automatic Flow Regulators for Flow Modulation During Blood Collection", the entire disclosure of which is hereby incorporated by reference.

BACKGROUND OF THE INVENTION

Field of the Invention

The present invention relates to flow regulators and, more particularly, automatic flow regulators for use during blood collection.

Description of Related Art

Needle assemblies are used for collecting specimens of fluid, such as blood, from a patient. Some such needle assemblies are intended for use with an evacuated tube and include a housing with a proximal end, a distal end, and a passage extending between the ends. Such needle assemblies further include at least one needle cannula mounted to the housing. The needle cannula includes a sharply pointed distal end that projects distally beyond the housing, a proximal end that projects proximally beyond the housing, and a lumen that provides communication between the opposed ends of the needle cannula. Some needle assemblies include separate proximal and distal cannulas and rely upon a portion of the housing to provide communication between the lumens of the respective cannulas. The distal end of the needle cannula typically is beveled to a tip that is sufficiently sharp for piercing the skin of the patient and accessing the vein or other source of fluid that is to be collected. The proximal end of the needle cannula is configured for piercing the rubber stopper on an evacuated tube. The proximal end of the needle cannula typically is covered by a needle pierceable resealable multi-sample sleeve. The sleeve is compressed by the rubber stopper of the evacuated tube and punctured by the proximal end of the needle cannula as the proximal end of the needle cannula is urged into communication with the evacuated tube. The evacuated tube is typically received by a needle holder secured to the proximal end of the housing.

The combined needle assembly and evacuated tube is employed by initially urging the pointed distal end of the needle cannula into a blood vessel of a patient. Once the targeted blood vessel has been accessed, the evacuated tube is urged into the needle holder such that the proximal point of the needle cannula pierces the septum of the tube. Low pressure conditions within the evacuated tube, as well as the patient's own vasculature pressure, generate a flow of blood from the patient through the needle cannula and into the evacuated tube. The evacuated tube may be removed from the needle holder after a sufficient quantity of blood has been collected. One or more additional evacuated tubes may similarly be urged into the open end of the needle holder for drawing one or more additional samples of blood to be analyzed. The needle cannula is then withdrawn from the patient after a sufficient volume of blood has been collected for the required analytical procedure.

During certain blood collection procedures, vein collapse of the patient occurs as a result of blood being removed too quickly from the patient's vein. Physiological conditions, such as elasticity of the vein wall, can contribute to this issue. With a conventional evacuated tube, there is a substantially instantaneous introduction of a vacuum pressure when the evacuated tube is attached to the non-patient end of the needle assembly or blood collection device. This strong vacuum pressure results in an initially high flow rate of blood out of the patient's vein. This abrupt outflow of blood coupled with the high elasticity of a patient's vein can lead to the vein wall being pulled down onto the cannula bevel and result in flow stoppage. Blood supply can also be a contributing factor of vein collapse. Most typical blood collection sites are in the patient's arm and hand. With these collection sites, the supply of blood available for collection resides below the collection side due to the one-way valves of the vein. In-flow of new blood to this area is limited as a result of the capillary blood vessels. In situations where there is limited resident blood, such as a hand collection site, the vacuum from the collection tube leads to a high flow rate out of the vein, which can lead to an outflow rate higher than the inflow rate of blood and a rapid depletion of the resident blood thereby leading to vein collapse.

With patients that are susceptible to vein collapse, syringes are commonly used for blood collection to provide the user with better control over the flow rate of blood out of the patient. However, the skill of the technician generally plays a large role in successfully using a syringe in a blood collection procedure. For instance, there can be a lot of variability in the amount of force the user exerts on the syringe plunger and the associated flow rates. Further, if not used appropriately, the syringe can achieve greater flow rates than a standard evacuated tube.

SUMMARY OF THE INVENTION

In accordance with an embodiment of the present invention, a flow regulator for a blood collection assembly includes a housing having an inlet and an outlet defining an interior space between the inlet and the outlet. The flow regulator includes a membrane having a first surface and a second surface disposed at least partially within the interior space. The membrane has a first position wherein a flow path between the inlet and the outlet is substantially open, and a second position wherein the flow path between the inlet and the outlet is at least partially restricted, with the membrane configured to move between the first and second positions in response to a pressure differential acting on the membrane.

In certain configurations, the pressure differential is generated by a first pressure acting on the first surface of the membrane and a second pressure acting on the second surface of the membrane, the first pressure greater than the second pressure. The inlet of the housing may include one of a male luer fitting and a female luer fitting, and the outlet of the housing may include the other of the male luer fitting and the female luer fitting. The membrane may have a projection extending from the membrane and an opening defined within the membrane in fluid communication with the inlet and the outlet. The opening may include a plurality of openings radially spaced from the projection. The membrane may include a plurality of flexible tabs disposed between the plurality of openings and the projection may have a frusto-conical shape.

The housing may include a tapered portion having a shape substantially corresponding to the frusto-conical shaped projection, and a distance between the tapered portion of the housing and an outer surface of the frusto-conical shaped projection may be smaller when the membrane is in the second position than when the membrane is in the first position. A portion of the frusto-conical shaped projection may be positioned adjacent to the housing to at least partially restrict the flow path extending between the inlet and the outlet of the housing when the membrane is in the second position. The inlet of the housing may include one of a male luer fitting and a female luer fitting, and the outlet of the housing may include the other of the male luer fitting and the female luer fitting.

The membrane may be secured to the housing by a plurality of flexible tabs. The membrane may also include a body defining an opening therethrough and a valve member extending from the body towards the outlet of the housing, with the valve member advanced at least partially into the outlet to at least partially restrict the flow path when the membrane is in the second position. The membrane may be configured to move between the first and second positions based on a pressure differential acting on the first surface and the second surface of the membrane. The housing may include first and second portions, with a perimeter of the membrane secured between the first and second portions of the housing.

A body of the valve member may include a tapered portion with a truncated profile adjacent the outlet. The inlet of the housing may include one of a male luer fitting and a female luer fitting, and with the outlet of the housing including the other of the male luer fitting and the female luer fitting. The membrane may include a body having a convex surface and a concave surface, with the membrane configured to move between the first and second positions based on a pressure differential acting on the convex surface and the concave surface of the body of the membrane. The concave surface of the body of the membrane may face the outlet of the housing, and the membrane may be biased when the membrane is in the second position. The membrane may be biased into the flow path in the second position.

The housing may include a membrane seat configured to engage a portion of the membrane when the membrane is in the second position. The membrane seat may define a channel in fluid communication with the outlet of the housing, with the channel at least partially restricting flow between the inlet and the outlet of the housing when the membrane is in the second position. The housing may include first and second portions, and the membrane seat may be provided on a second portion of the housing. The inlet of the housing may include one of a male luer fitting and a female luer fitting, and the outlet of the housing may include the other of the male luer fitting and the female luer fitting.

The flow regulator may also include a valve body positioned within the interior space and defining a passageway, with the membrane including a body and a plurality of flexible tabs extending radially outward from the body, with the plurality of flexible tabs securing the membrane to the valve body. The membrane may be positioned within the passageway of the valve body. The valve body may have a first end secured to the housing and a second end configured to receive a tube. The membrane and the valve body may define a plurality of openings between the plurality of flexible tabs, with the plurality of openings providing a flow passageway between the inlet and the outlet of the housing.

The housing may include a membrane seat configured to engage the membrane when the membrane is in the second position. The membrane seat may define a channel that is in fluid communication with the outlet of the housing, with the channel partially restricting flow between the inlet and the outlet of the housing when the membrane is in the second position. The membrane may include a body defining an opening therethrough, the body of the membrane having a convex surface and a concave surface. The convex surface of the membrane may face the outlet of the housing, and the membrane may be configured to move between the first and second positions in response to a pressure differential acting on the convex surface and the concave surface of the membrane.

The flow regulator may also include a spherical shaped projection positioned between the membrane and the outlet of the housing, with the projection engaging the housing and the membrane when the membrane is in the first and second positions. The housing may include a membrane seat configured to engage the membrane when the membrane is in the second position, with the membrane seat defining a channel that is in fluid communication with the outlet of the housing. The channel may at least partially restrict flow between the inlet and the outlet of the housing when the membrane is in the second position.

In accordance with another embodiment of the present invention, a flow regulator for a blood collection assembly includes a housing having an inlet and an outlet and defining an interior space between the inlet and the outlet, with the interior space having an inlet side and an outlet side. The flow regulator may also include a valve positioned within the interior space, the valve having a base secured to the housing and a valve member secured to the base via a flexible member, the valve member having a first position wherein a flow path between the inlet and the outlet is substantially open and a second position wherein the flow path between the inlet and the outlet is at least partially restricted. The valve member may be configured to move between the first and second positions based on a pressure differential acting on an inlet side of the valve member and an outlet side of the valve member.

The base of the valve may include a ring-shaped body having a support that is secured to the flexible member. The valve member may also include a spherical body. The flexible member may include an elastic material having a first length when the valve member is in the first position and a second length when the valve member is in the second position. The inlet of the housing may include one of a male luer fitting and a female luer fitting, with the outlet of the housing including the other of the male luer fitting and the female luer fitting.

In accordance with yet another embodiment, a flow regulator for a blood collection assembly includes a housing having an inlet and an outlet and defining an interior space between the inlet and the outlet, with the housing having a valve seat. The flow regulator also includes a valve member having a first surface and a second surface, the valve member positioned within the interior space and secured to the housing via a flexible hinge. The valve member includes a first position wherein a flow path between the inlet and the outlet is substantially open, and a second position wherein the valve member is at least partially disposed over the outlet to at least partially restrict the flow path between the inlet and the outlet. The valve member is configured to move between the first and second positions based on a pressure differential acting on the first surface of the valve member and the second surface of the valve member.

The valve member may be spaced from the valve seat when the valve member is in the first position, and the valve member may engage the valve seat when the valve member is in the second position. The housing may include a needle holder configured to receive an evacuated container. The needle holder may include a cannula having a proximal end and a distal end, with the valve member aligned with the distal end of the cannula.

In accordance with still a further embodiment, a flow regulator for a blood collection assembly includes a housing having an inlet and an outlet and defining an interior space between the inlet and the outlet, the interior space having an inlet side and an outlet side, and the housing having a valve seat that defines a channel in fluid communication with the outlet. The flow regulator further includes a valve member positioned within the interior space, with the valve member having a first position wherein a flow path between the inlet and the outlet is substantially open and a second position wherein the flow path between the inlet and the outlet is partially restricted. The valve member is configured to move between the first and second positions in response to a pressure differential acting on the inlet side of the valve member and the outlet side of the valve member.

The valve member may engage the valve seat when the valve member is in the second position, and the channel of the valve seat is configured to partially restrict flow between the inlet and the outlet of the housing when the valve member is in the second position. The valve member may include a spherical body.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIG. 7 is rear view of the flow regulator of FIG. 4 in accordance with an embodiment of the present invention.

FIG. 8 is cross-sectional view of the flow regulator taken along line 8-8 in FIG. 7 in accordance with an embodiment of the present invention.

FIG. 9 is a perspective view of a membrane utilized in connection with the flow regulator of FIG. 4 in accordance with an embodiment of the present invention.

FIG. 12 is a cross-sectional view of a flow regulator showing a first position of the flow regulator according to a second embodiment of the present invention.

FIG. 13 is a cross-sectional view of the flow regulator of FIG. 12 showing a second position of the flow regulator in accordance with an embodiment of the present invention.

FIG. 14 is a cross-sectional view of a flow regulator showing a first position of the flow regulator according to a third embodiment of the present invention.

FIG. 15 is a cross-sectional view of the flow regulator of FIG. 14 showing a second position of the flow regulator in accordance with an embodiment of the present invention.

FIG. 16 is a perspective view of a membrane utilized in connection with the flow regulator of FIG. 14 in accordance with an embodiment of the present invention.

FIG. 17 is a cross-sectional view of a flow regulator showing a first position of the flow regulator according to a fourth embodiment of the present invention.

FIG. 18 is a cross-sectional view of the flow regulator of FIG. 17 showing a second position of the flow regulator in accordance with an embodiment of the present invention.

FIG. 19 is a perspective view of a valve member utilized in connection with the flow regulator of FIG. 17 in accordance with an embodiment of the present invention.

FIG. 20 is a cross-sectional view of a flow regulator showing a first position of the flow regulator according to a fifth embodiment of the present invention.

FIG. 21 is a cross-sectional view of the flow regulator of FIG. 20 showing a second position of the flow regulator in accordance with an embodiment of the present invention.

FIG. 22 is a perspective view of a membrane utilized in connection with the flow regulator of FIG. 20 in accordance with an embodiment of the present invention.

FIG. 27 is an exploded view of the blood collection set of FIG. 25 in accordance with an embodiment of the present invention.

FIG. 28 is a perspective view of a flow regulator utilized in connection with the blood collection set of FIG. 25 in accordance with an embodiment of the present invention.

FIG. 29 is a side view of the flow regulator of FIG. 28 in accordance with an embodiment of the present invention.

FIG. 30 is front view of the flow regulator of FIG. 28 in accordance with an embodiment of the present invention.

DETAILED DESCRIPTION OF THE EMBODIMENTS

Figure 1:
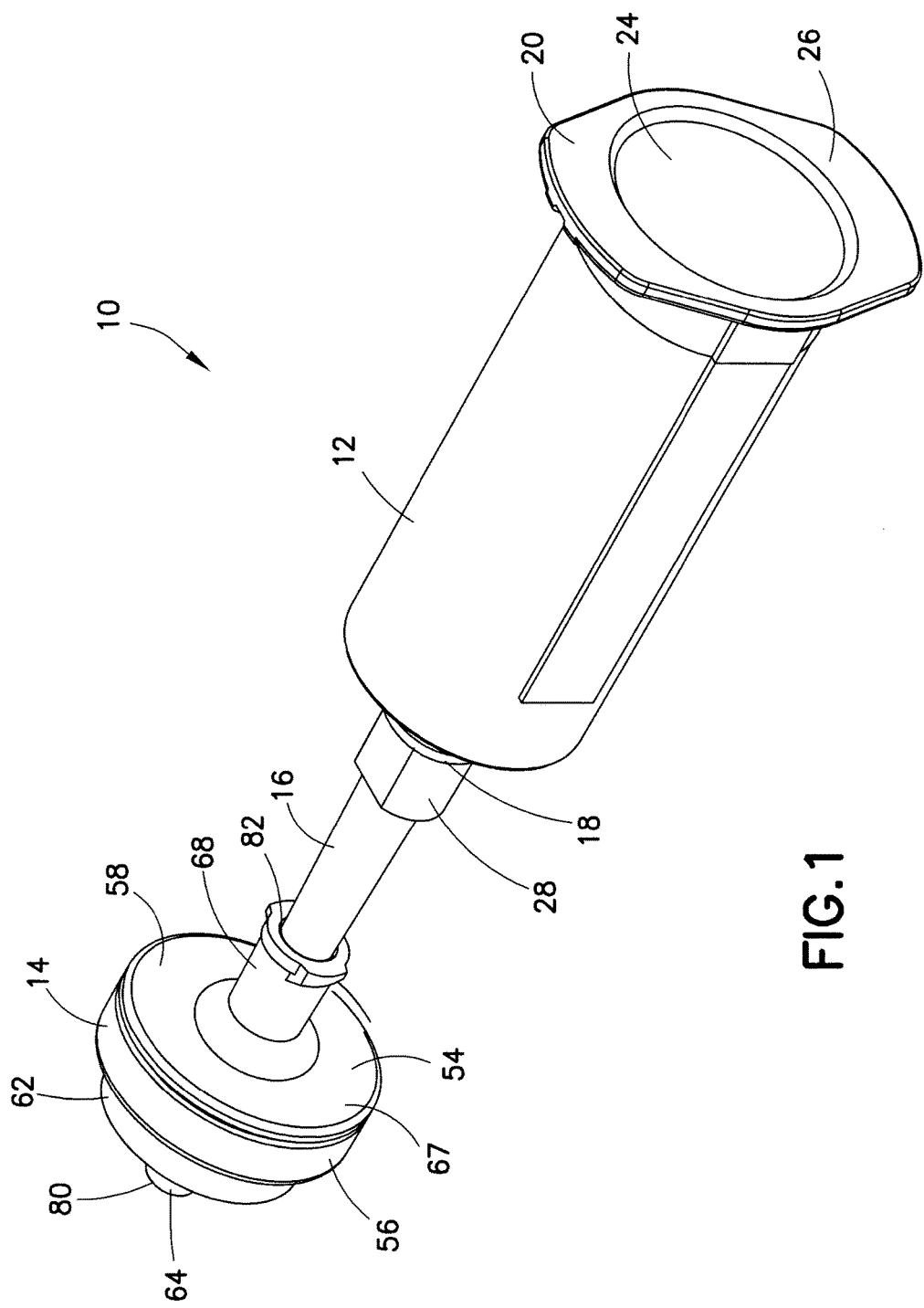
FIG. 1 is a perspective view of a blood collection set with a flow regulator according to one embodiment of the present invention.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Referring to FIGS. 1-11, one embodiment of a blood collection set 10 includes a needle holder 12, a flow regulator 14, and a connector tube 16. The needle holder 12 has a first or distal end 18 and a second or proximal end 20 and includes a generally cylindrical-shaped sidewall 22 extending between the first and second ends 18, 20. The sidewall 22 may be formed from a transparent or translucent plastic material and defines an interior space 24 between the first and second ends 18, 20. The needle holder 12 has a flange 26 extending radially outward from the sidewall 22 at a position adjacent to the second end 20. The needle holder 12 further includes an adapter 28 secured to the first end 18 of the needle holder 12. The adapter 28 includes a first or distal end 30 and a second or proximal end 32 with a passageway 34 extending longitudinally between the first and second ends 30, 32. The adapter 28 has a receiving portion 36 positioned adjacent to the first end 30, a threaded portion 38 positioned adjacent to the second end 32, and a flange 40 extending radially outward and positioned between the receiving portion 36 and the threaded portion 38. The receiving portion 36 of the adapter 28 is configured to receive an end of a tube, although the receiving portion may also be configured to receive a female or male luer fitting. The threaded portion 38 of the adapter 28 is configured to engage a corresponding threaded portion 42 of the first end 18 of the needle holder 12. The second end 32 of the adapter 28 receives a cannula 44 with a first or distal end 46, a second or proximal end 48, and a lumen extending between the ends 46, 48. The cannula 44 includes a proximal tip 52 that is configured to pierce an evacuated tube.

Referring to FIGS. 4-9, the flow regulator 14 includes a housing 54 having a first portion 56 and a second portion 58 with the first portion 56 secured to the second portion 58 to define an interior space 60. The first portion 56 of the flow regulator 14 includes a body 62 having a male luer fitting 64 and a flange 66 extending radially outward from the body 62 of the first portion 56. The second portion 58 of the flow regulator 14 includes a body 67 having a female luer fitting 68 and a flange 70 extending radially outward from the body 67 of the second portion 58. The flange 70 of the second portion 58 of the flow regulator 14 also includes a tapered portion 72 that defines a tapered inner surface 74 within the interior space 60. Although the first and second portions 56, 58 of the flow regulator 14 include male and female luer fittings 64, 68, the first and second portions 56, 58 may include other suitable securing arrangements conventionally utilized in connection with blood collection sets. The first and second portions 56, 58 of the flow regulator 14 each include an annular ring 76, 78 extending from the respective flanges 66, 70. The annular rings 76, 78 of the first and second portions 56, 58 are configured to engage each other via a friction or interference fit to secure the first portion 56 to the second portion 58, although other suitable arrangements for securing the first portion 56 to the second portion 58 may be utilized. The first portion 56 of the flow regulator 14 includes an inlet 80 and the second portion 58 of the flow regulator 14 includes an outlet 82 with a flow passageway 84 extending through the flow regulator 14 between the inlet 80 and the outlet 82.

Referring again to FIGS. 4-9, the flow regulator 14 further includes a membrane 86 positioned within the interior space 60 and aligned with the flow passageway 84 of the flow regulator 14. The membrane 86 has a body 88 with a first surface 90 and a second surface 92 that defines a plurality of openings 94 extending through the body 88 from the first surface 90 to the second surface 92. The membrane 86 includes an annular flange 96 at a circumferential edge of the membrane 86. The membrane 86 further includes a valve member 98 extending outward from the second surface 92 of the membrane 86. The valve member 98 includes a first generally cylindrical portion 102 extending from the second surface 92 of the membrane 86, a tapered portion 104 extending from the first cylindrical portion 102, and a second generally cylindrical portion 106 extending from the tapered portion 104. The first surface 90 of the membrane 86 defines a recessed portion 108 at a position opposite from the valve member 98. A perimeter of the membrane 86 is secured to the first and second portions 56, 58 of the housing 54. In particular, when the flow regulator 14 is assembled, annular securing projections 110, 112 provided on each of the first and second portions 56, 58 of the housing 54 engage a portion of the membrane radially inward from the flange 96 of the membrane 86. The flange 96 of membrane 86 is positioned between the annular rings 76, 78 and the annular securing projections 110, 112 of the first and second portions 56, 58 of the housing 54 such that membrane 86 is securely positioned within the interior space 60 and aligned with the flow passageway 84 of the flow regulator 14. The membrane 86 is formed from an elastomeric material and is configured to deflect in response to a difference in pressure acting on the first and second surface 90, 92 of the membrane 86 as will be discussed in more detail below.

Figure 2:
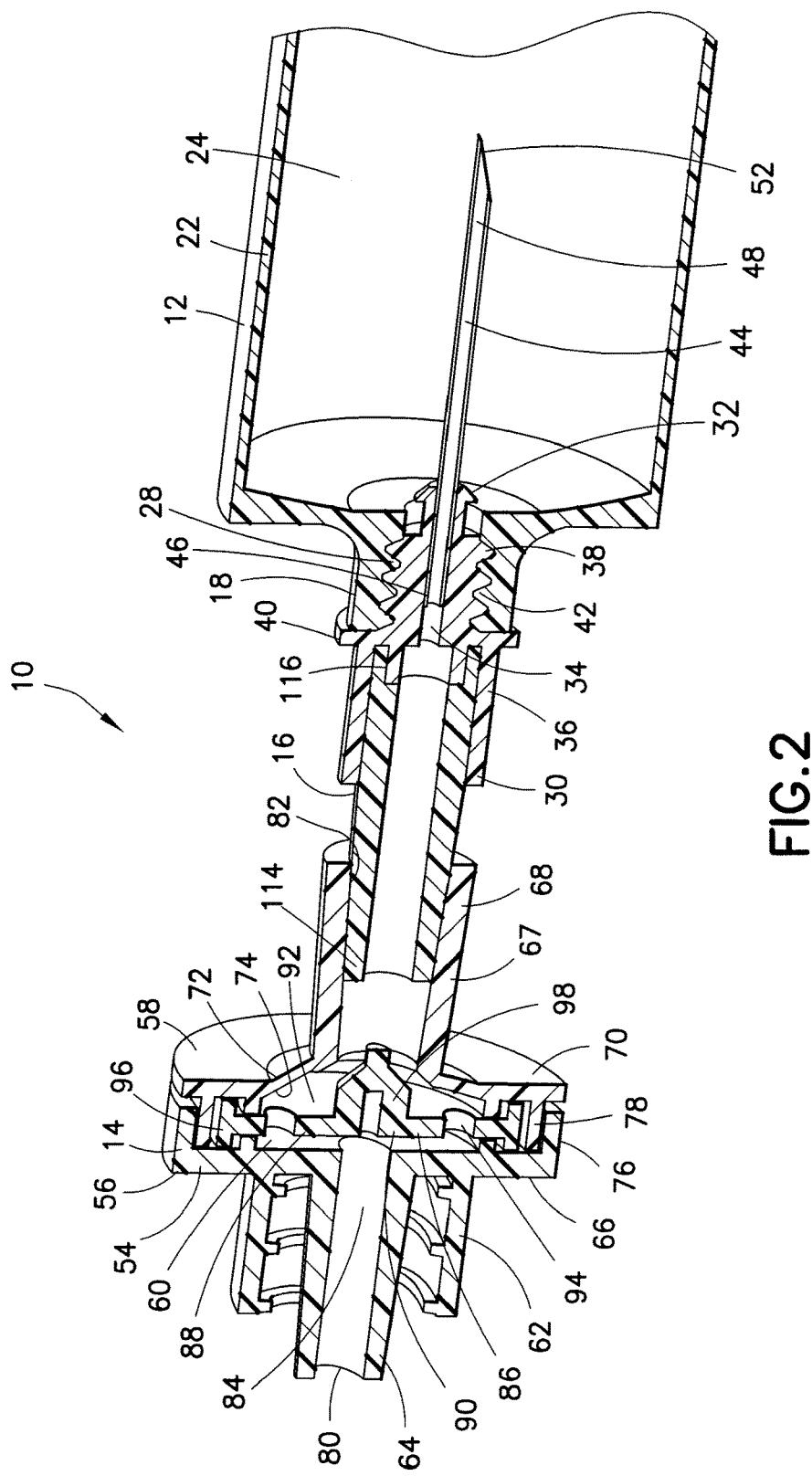
FIG. 2 is a cross-sectional view of the blood collection set of FIG. 1 in accordance with an embodiment of the present invention.
Figure 3:
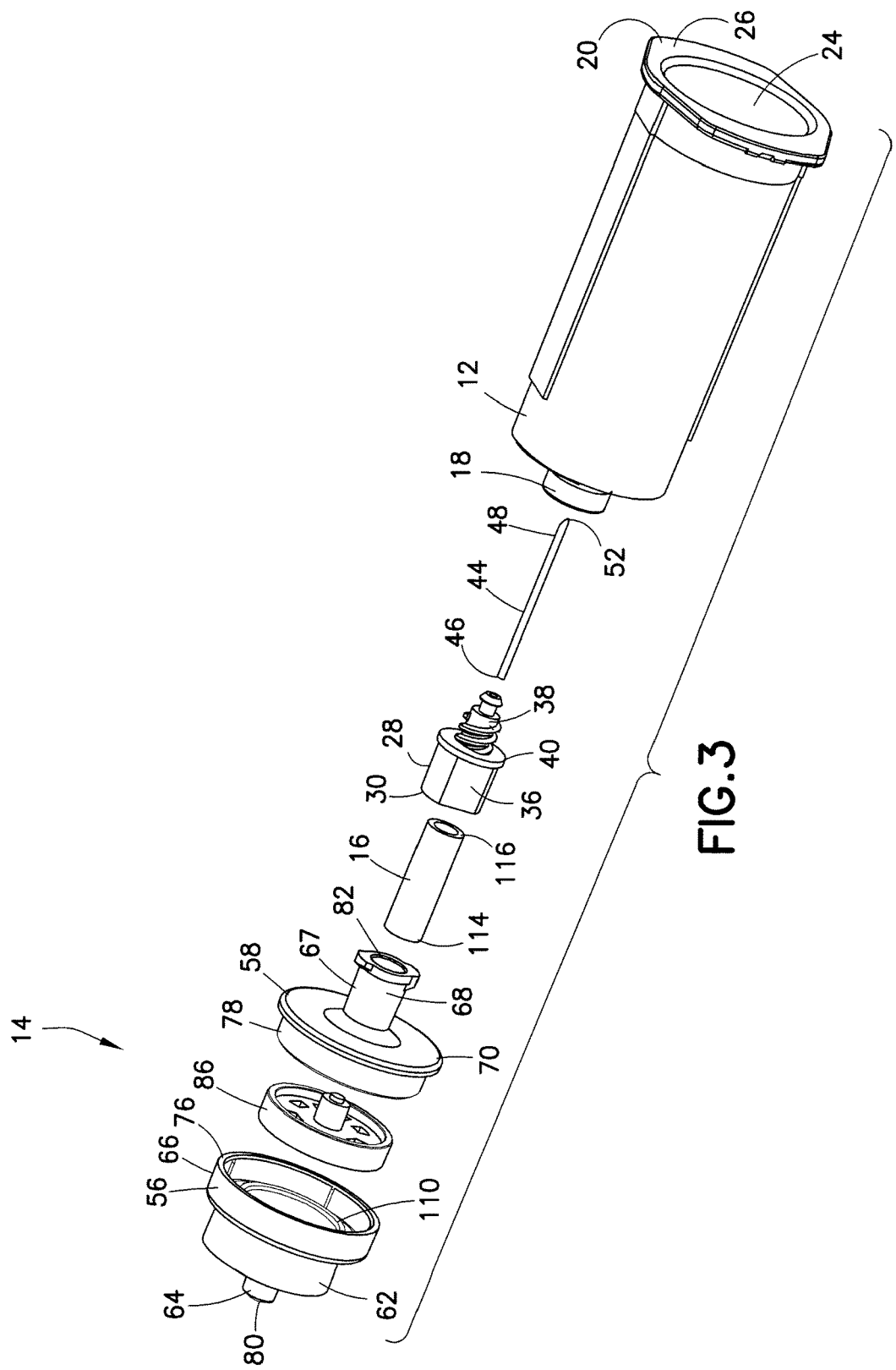
FIG. 3 is an exploded view of the blood collection set of FIG. 1 in accordance with an embodiment of the present invention.
Figure 4:
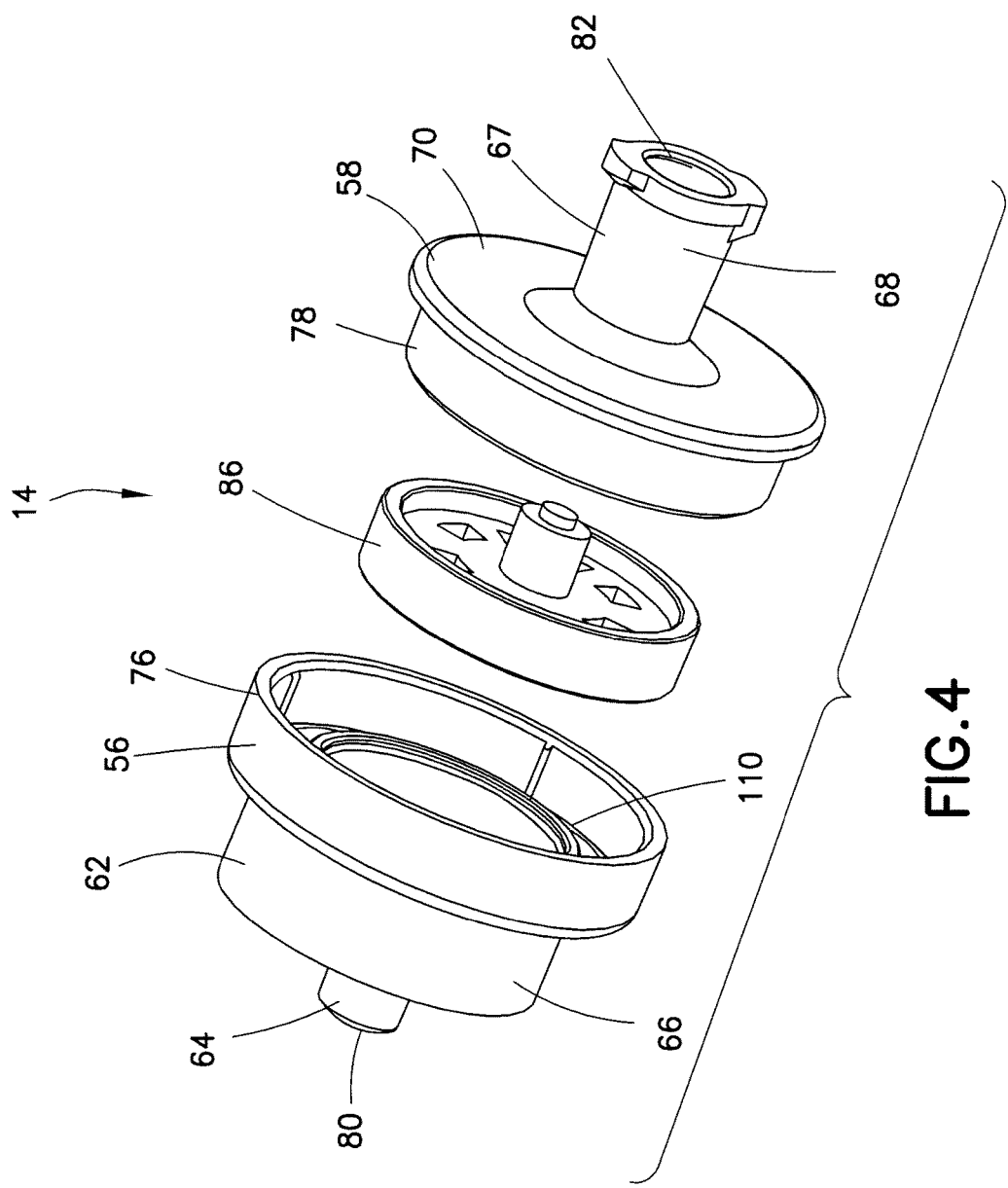
FIG. 4 is a perspective view of a flow regulator utilized in connection with the blood collection set of FIG. 1 in accordance with an embodiment of the present invention.
Figure 5:
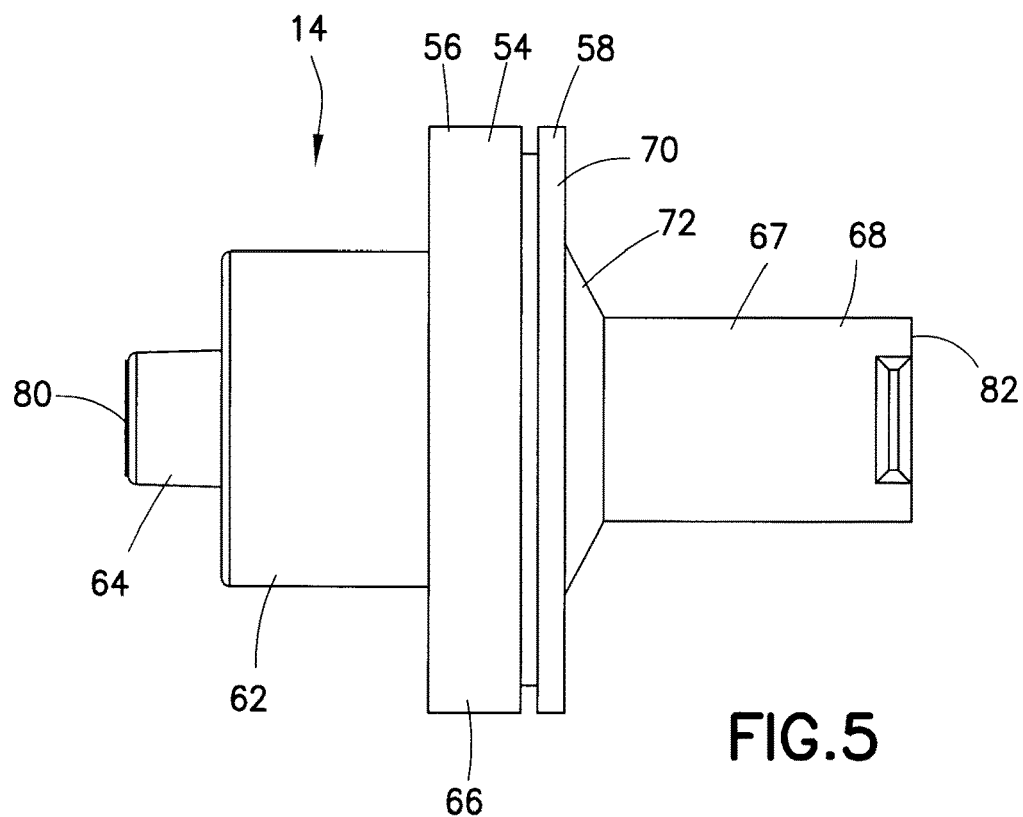
FIG. 5 is a side view of the flow regulator of FIG. 4 in accordance with an embodiment of the present invention.
Figure 6:
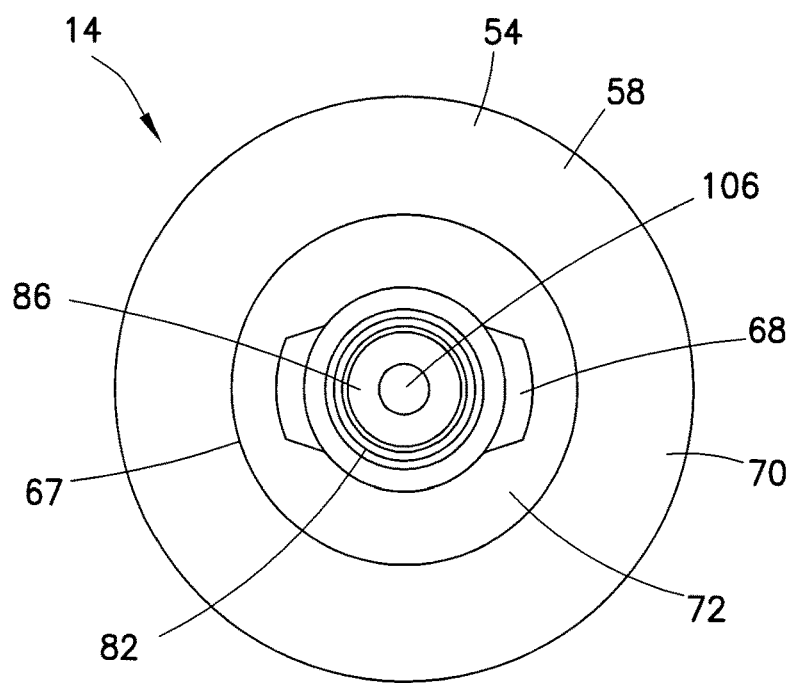
FIG. 6 is front view of the flow regulator of FIG. 4 in accordance with an embodiment of the present invention.

Referring to FIGS. 1-3, the blood collection set 10 is assembled by securing a first end 114 of the connector tube 16 to the female luer fitting 68 of the flow regulator 14. A second end 116 of the connector tube 16 is secured to the receiving portion 36 of the adaptor 28 of the needle holder 12. The male luer fitting 64 of the flow regulator 14 is secured to a wing set or needle assembly (not shown), which is configured to pierce a targeted blood vessel of a patient. Although the flow regulator 14 is shown connected to the needle holder via the connector tube 16, the flow regulator 14 may also be directly secured to the needle holder 12 through any suitable connection or may be formed integrally with the needle holder 12. In use, a phlebotomist guides the wing set or needle assembly of the blood collection set 10 into a targeted blood vessel. After access to the blood vessel has been attained, the phlebotomist inserts an evacuated tube (not shown) into the needle holder 12 with fluid flowing from the wing set or needle assembly through the flow regulator 14, through the cannula 44 of the needle holder 12, and into the evacuated tube. More specifically, fluid flows through the inlet 80 of the flow regulator 14 through the openings 94 of the membrane 86 and through the outlet 82 of the flow regulator 14.

Figure 10:
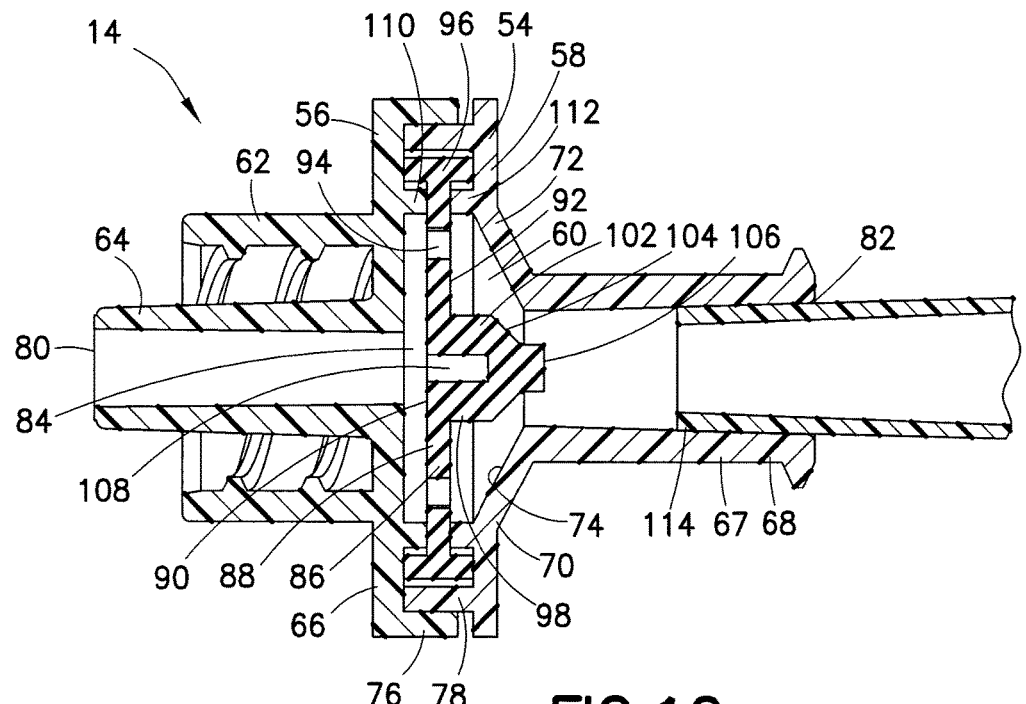
FIG. 10 is a partial cross-sectional view of the blood collection set of FIG. 1 showing a first position of the flow regulator in accordance with an embodiment of the present invention.
Figure 11:
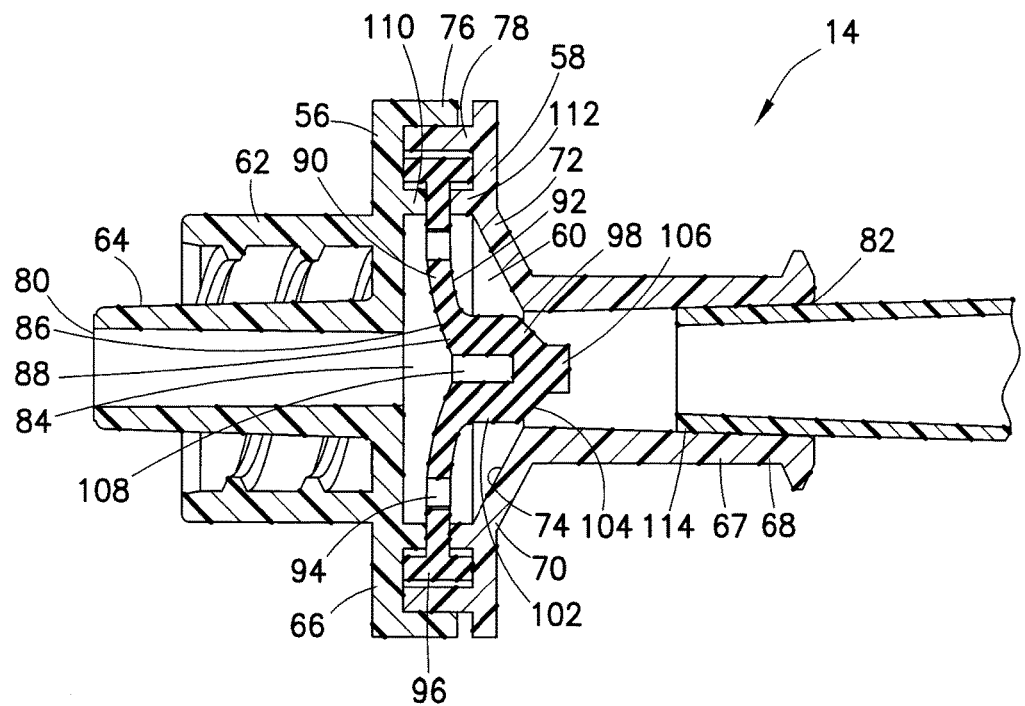
FIG. 11 is a partial cross-sectional view of the blood collection set of FIG. 1 showing a second position of the regulator in accordance with an embodiment of the present invention.

Referring to FIGS. 10 and 11, the membrane 86 of the flow regulator 14 has a first position (shown in FIG. 10) where the flow passageway 84 between the inlet 80 and the outlet 82 of the flow regulator 14 is substantially open, and a second position (shown in FIG. 11) where the membrane 86 is deflected and the valve member 98 of the membrane 86 is advanced at least partially into the outlet 82 to at least partially restrict the flow passageway 84. The flow regulator 14 is configured to automatically vary the geometry of the flow passageway 84 during the fluid collection procedure to actively control the flow rate through the flow regulator 14. In particular, at the beginning of the collection process when the evacuated tube is secured to the needle holder 12, the pressure differential between the inlet 80 and outlet 82 of the flow regulator 14 is greatest with a negative pressure from the evacuated tube acting on the second surface 92 of the membrane 86 and a positive pressure from the fluid flowing from the patient acting on the first surface 90 of the membrane 86. In such a condition, the membrane 86 will deflect to the position shown in FIG. 11 with the valve member 98 partially restricting the flow passageway 84 such that the flow rate through the flow regulator 14 is reduced. The tapered inner surface 74 of the second portion 58 of the housing 54 and the tapered portion 104 of the valve member 98 cooperate to act as a needle valve to meter flow from the inlet 80 to the outlet 82. As the fluid collection proceeds, the pressure within the evacuated tube increases such that the pressure differential between the first surface 90 and the second surface 92 of the membrane 86 is reduced.

When the difference in pressures acting on the first surface 90 and the second surface 92 of the membrane 86 is reduced to a predetermined value, the membrane 86 will return to the position shown in FIG. 10 with the flow passageway 84 substantially open such that the flow rate through the flow regulator 14 is increased relative to when the membrane 86 is in the second position shown in FIG. 11. The thickness and elasticity of the membrane 86 may be selected such that the membrane 86 moves from the first position towards the second position when a predetermined difference in the pressures acting on the first surface 90 of the membrane 86 and the second surface 92 of the membrane 86 is reached. Thus, the membrane 86 can be designed to move between the first position and the second position to control the geometry of the flow passageway 84 and the flow rate through the flow regulator 14 for a range of pressures acting on the membrane 86.

Referring to FIGS. 12 and 13, a second embodiment of a flow regulator 130, which is similar to the flow regulator 14 shown in FIGS. 1-11 and described above, includes a housing 132 having a first portion 134 and a second portion 136 with the first portion 134 secured to the second portion 136 to define an interior space 138. The first portion 134 of the flow regulator 130 includes a body 140 having a male luer fitting 142 and a flange 144 extending radially outward from the body 140 of the first portion 134. The second portion 136 of the flow regulator 130 includes a body 146 having a female luer fitting 148 and a flange 150 extending radially outward from the body 146 of the second portion 136. The flange 150 of the second portion 136 of the flow regulator 130 also includes a tapered portion 152 that defines a tapered inner surface 154 within the interior space 138. Although the first and second portions 134, 136 of the flow regulator 130 include male and female luer fittings 142, 148, the first and second portions 134, 136 may include other suitable securing arrangements conventionally utilized in connection with blood collection sets. The first and second portions 134, 136 of the flow regulator 130 each include an annular ring 156, 158 extending from the respective flanges 144, 150. The annular rings 156, 158 of the first and second portions 134, 136 are configured to engage each other to secure the first portion 134 to the second portion 136. The annular rings 156, 158 of the first and second portions 134, 136 may be secured to each other via an adhesive, although other suitable arrangements for securing the first portion 134 to the second portion 136 may be utilized. The first portion 134 of the flow regulator 130 includes an inlet 160 and the second portion 136 of the flow regulator 130 includes an outlet 162 with a flow passageway 164 extending through the flow regulator 130 between the inlet 160 and the outlet 162.

Referring again to FIGS. 12 and 13, the flow regulator 130 further includes a membrane 166 positioned within the interior space 138 and aligned with the flow passageway 164 of the flow regulator 130. The membrane 166 has a body 168 with a first surface 170 and a second surface 172 that defines a plurality of openings 174 extending through the body 168 from the first surface 170 to the second surface 172. The membrane 166 includes an annular flange 176 at a circumferential edge of the membrane 166. The membrane 166 further includes a valve member 178 extending outward from the second surface 172 of the membrane 166. The valve member 178 includes a first generally cylindrical portion 180 extending from the second surface 172 of the membrane 166, a tapered portion 182 extending from the first cylindrical portion 180, and a second generally cylindrical portion 184 extending from the tapered portion 182. Relative to the membrane 86 of FIGS. 1-11, the membrane 166 of the present embodiment is positioned closer to the inlet 160 of the flow regulator 130 and the first generally cylindrical portion 180 of the membrane 166 is longer. Annular securing projections 186, 188 provided on each of the first and second portions 134, 136 of the housing 132 engage a portion of the membrane 166 radially inward from the flange 176 of the membrane 166. The flange 176 of membrane 166 is positioned between the annular rings 156, 158 and the annular securing projections 186, 188 of the first and second portions 134, 136 of the housing 132 such that membrane 166 is securely positioned within the interior space 138 and aligned with the flow passageway 164 of the flow regulator 130.

The membrane 166 of the flow regulator 130 has first position (shown in FIG. 12) where the flow passageway 164 between the inlet 160 and the outlet 162 of the flow regulator 130 is substantially open, and a second position (shown in FIG. 13) where the membrane 166 is deflected and the valve member 178 of the membrane 166 is advanced at least partially into the outlet 162 to at least partially restrict the flow passageway 164. The flow regulator 130 operates in the same manner as the flow regulator 14 discussed above in connection with FIGS. 1-11. Further, the inlet 160 of the flow regulator 130 may be secured to a wing set or needle assembly (not shown) and the outlet 162 of the flow regulator 130 may be secured to a needle holder (not shown) as discussed above in connection with FIGS. 1-11.

Referring to FIGS. 14-16, a third embodiment of a flow regulator 200 includes a housing 202 having a first portion 204 and a second portion 206 with the first portion 204 secured to the second portion 206 to define an interior space 207. The first portion 204 of the flow regulator 200 includes a body 208 having a male luer fitting 210 and a flange 212 extending radially outward from the body 208 of the first portion 204. The second portion 206 of the flow regulator 200 includes a body 214 having a female luer fitting 216 and a flange 218 extending radially outward from the body 214 of the second portion 206. The flange 218 of the second portion 206 of the flow regulator 200 also includes a tapered portion 220 that defines a tapered inner surface 222 within the interior space 207. Although the first and second portions 204, 206 of the flow regulator 200 include male and female luer fittings 210, 216, the first and second portions 204, 206 may include other suitable securing arrangements conventionally utilized in connection with blood collection sets. The first portion 204 of the flow regulator 200 includes an inlet 224 and the second portion 206 of the flow regulator 200 includes an outlet 226 with a flow passageway 228 extending through the flow regulator 200 between the inlet 224 and the outlet 226.

Referring again to FIGS. 14-16, the flow regulator 200 further includes a membrane 230 positioned within the interior space 207 and aligned with the flow passageway 228 of the flow regulator 200. The membrane 230 has a first surface 232 and a second surface 234 and a projection 236 extending from the second surface 234 of the membrane 230. The projection 236 has a frusto-conical shape substantially corresponding to the shape of the tapered inner surface 222 of the second portion 206 of the housing 202. The membrane 230 also includes a plurality of flexible tabs 238 extending radially outward and securing the membrane 230 to the housing 202. The membrane 230 defines a plurality of openings 240 between the flexible tabs 238. The membrane 230 of the flow regulator 200 has a first position (shown in FIG. 14) where the flow passageway 228 between the inlet 224 and the outlet 226 of the flow regulator 200 is substantially open, and a second position (shown in FIG. 15) where the membrane 230 is deflected and the flow passageway 228 between the inlet 224 and the outlet 226 is at least partially restricted. The projection 236 of the membrane 230 is advanced such that a distance between the tapered inner surface 222 of the housing 202 and an outer surface of the projection 236 is smaller when the membrane 230 is in the second position than when the membrane 230 is in the first position. Thus, the projection 236 of the membrane 230 is configured to restrict flow through the flow passageway 228 as the membrane 230 moves from the first position to the second position. The membrane 230 moves between the first position and the second position in response to a pressure differential acting on the first and second surfaces 232, 234 of the membrane 230 in the same manner as discussed above in connection with FIGS. 1-11. Further, the inlet 224 of the flow regulator 200 may be secured to a wing set or needle assembly (not shown) and the outlet 226 of the flow regulator 200 may be secured to a needle holder (not shown) as discussed above in connection with FIGS. 1-11.

Referring to FIGS. 17-19, a fourth embodiment of a flow regulator 250 includes a housing 252 having a first portion 254 and a second portion 256 with the first portion 254 secured to the second portion 256 to define an interior space 258. The first portion 254 of the flow regulator 250 includes a body 260 having a male luer fitting 262 and a flange 264 extending radially outward from the body 260 of the first portion 254. The second portion 256 of the flow regulator 250 includes a body 266 having a female luer fitting 268 and a flange 270 extending radially outward from the body 266 of the second portion 256. Although the first and second portions 254, 256 of the flow regulator 250 include male and female luer fittings 262, 268, the first and second portions 254, 256 may include other suitable securing arrangements conventionally utilized in connection with blood collection sets. The first portion 254 of the flow regulator 250 includes an inlet 272 and the second portion 256 of the flow regulator 250 includes an outlet 274 with a flow passageway 276 extending through the flow regulator 250 between the inlet 272 and the outlet 274. The interior space 258 of the flow regulator 250 has an inlet side 278 and an outlet side 280.

Referring again to FIGS. 17-19, the flow regulator 250 further includes a valve 282 positioned within the interior space 258. The valve 282 has a base 284 secured to the housing 252 and positioned adjacent to the respective flanges 264, 270 of the first and second portions 254, 256 of the housing 252. The valve 282 also includes a valve member 286 secured to the base 284 via a flexible member 288. The base 284 of the valve 282 has a ring-shaped body 289 having a central support 290 secured to the body 289 via a plurality of spokes 292. A first end 294 of the flexible member 288 is secured to the central support 290 of the base 284 with a second end 296 of the flexible member 288 secured to the valve member 286. The valve member 286 has a spherical-shaped body and the flexible member 288 has a rod-shaped body, although other suitable shapes may be utilized for the valve member 286 and the flexible member 288. The flexible member 288 is configured to stretch, i.e., change its effective length, and may be constructed from an elastomeric material.

The valve member 286 of the flow regulator 250 has a first position (shown in FIG. 17) where the flow passageway 276 between the inlet 272 and the outlet 274 of the flow regulator 250 is substantially open, and a second position (shown in FIG. 18) where the valve member 286 is at least partially disposed over the outlet 274 to at least partially restrict the flow passageway 276 between the inlet 272 and the outlet 274. When the valve member 286 is in the second position, the valve member 286 is closer to the outlet 274 relative to when the valve member 286 is in the first position such that flow through the flow passageway 276 is increasingly restricted as the valve member 286 moves from the first position to the second position. The valve member 286 is configured to move between the first position and the second position in response to a pressure differential acting on the inlet side 278 of the valve member 286 and the outlet side 280 of the valve member 286. The inlet 272 of the flow regulator 250 may be secured to a wing set or needle assembly (not shown) and the outlet 274 of the flow regulator 250 may be secured to a needle holder (not shown) as discussed above in connection with FIGS. 1-11.

Referring to FIGS. 20-22, a fifth embodiment of a flow regulator 300 includes a housing 302 having a first portion 304 and a second portion 306 with the first portion 304 secured to the second portion 306 to define an interior space 308. The first portion 304 of the flow regulator 300 includes a body 310 having a male luer fitting 312 and a flange 314 extending radially outward from the body 310 of the first portion 304. The second portion 306 of the flow regulator 300 includes a body 316 having a female luer fitting 318 and a flange 320 extending radially outward from the body 316 of the second portion 306. Although the first and second portions 304, 306 of the flow regulator 300 include male and female luer fittings 312, 318, the first and second portions 304, 306 may include other suitable securing arrangements conventionally utilized in connection with blood collection sets. The first and second portions 304, 306 of the flow regulator 300 each include an annular ring 322, 324 extending from the respective flanges 314, 320. The annular rings 322, 324 of the first and second portions 304, 306 are configured to engage each other via a friction or interference fit to secure the first portion 304 to the second portion 306, although other suitable arrangements for securing the first portion 304 to the second portion 306 may be utilized. The first portion 304 of the flow regulator 300 includes an inlet 326, and the second portion 306 of the flow regulator 300 includes an outlet 328 with a flow passageway 330 extending through the flow regulator 300 between the inlet 326 and the outlet 328. The second portion 306 of the housing 302 includes a generally annular membrane seat 332 positioned within the interior space 308 of the housing 302. The membrane seat 332 defines a channel 334 in fluid communication with the outlet 328, which is discussed in additional detail below.

Referring again to FIGS. 20-22, the flow regulator 300 further includes a membrane 336 positioned within the interior space 308 and aligned with the flow passageway 330 of the flow regulator 300. The membrane 336 has a body 338 with a convex surface 340 and a concave surface 342 positioned opposite the convex surface 340. The convex surface 340 faces the inlet 326 of the housing 302 and the concave surface 342 faces the outlet 328 of the housing 302. The body 338 of the membrane 336 defines a plurality of openings 344 extending through the body 338 from the convex surface 340 to the concave surface 342. The membrane 336 includes an annular flange 346 at a circumferential edge of the membrane 336. A perimeter of the membrane 336 is secured to the first and second portions 304, 306 of the housing 302 via annular securing projections 348, 350 provided on each of the first and second portions 304, 306 of the housing 302, which engage a portion of the membrane 336 radially inward from the flange 346 of the membrane 336. The flange 346 of membrane 336 is positioned between the annular rings 322, 324 and the annular securing projections 348, 350 of the first and second portions 304, 306 of the housing 302 such that membrane 336 is securely positioned within the interior space 308 and aligned with the flow passageway 330 of the flow regulator 300. The membrane 336 is formed from an elastomeric material and is configured to deflect in response to a difference in pressure acting on the convex and concave surfaces 340, 342 of the membrane 336 as will be discussed in more detail below.

The membrane 336 of the flow regulator 300 has a first position (shown in FIG. 20) where the flow passageway 330 between the inlet 326 and the outlet 328 of the flow regulator 300 is substantially open, and a second position (shown in FIG. 21) where the flow passageway 330 between the inlet 326 and outlet 328 is at least partially restricted. When the membrane 336 is in the second position, the membrane 336 engages the membrane seat 332 and is biased to form a substantially planar surface such that fluid flow from the inlet 326 must travel through the openings 344 in the membrane 336 and through the channel 334 of the membrane seat 332 to the outlet 328. Accordingly, when the membrane 336 is in the second position, the flow of fluid from the inlet 326 to the outlet 328 must pass through the channel 334 which partially restricts the flow between the inlet 326 and outlet 328. The membrane 336 is configured to move between the first position and the second position in response to a pressure differential acting on the convex surface 340 and the concave surface 342 of the body 338 of the membrane 336. The inlet 326 of the flow regulator 300 may be secured to a wing set or needle assembly (not shown) and the outlet 328 of the flow regulator 300 may be secured to a needle holder (not shown) as discussed above in connection with FIGS. 1-11.

Figure 24:
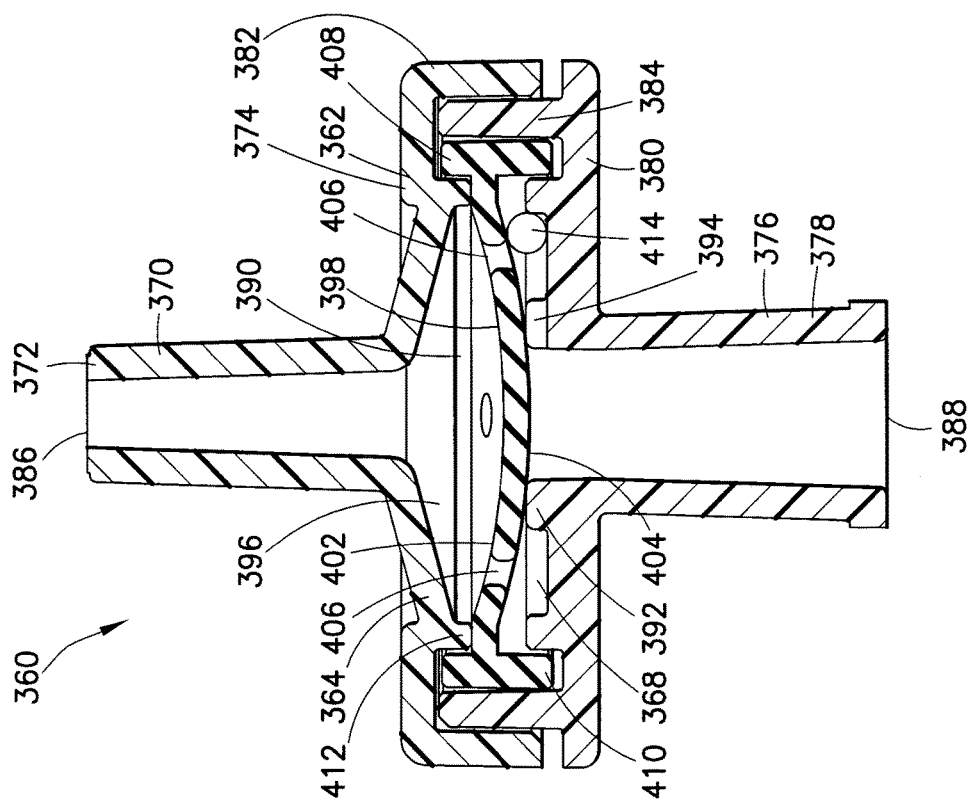
FIG. 24 is a cross-sectional view of the flow regulator of FIG. 23 showing a second position of the flow regulator in accordance with an embodiment of the present invention.
Figure 23:
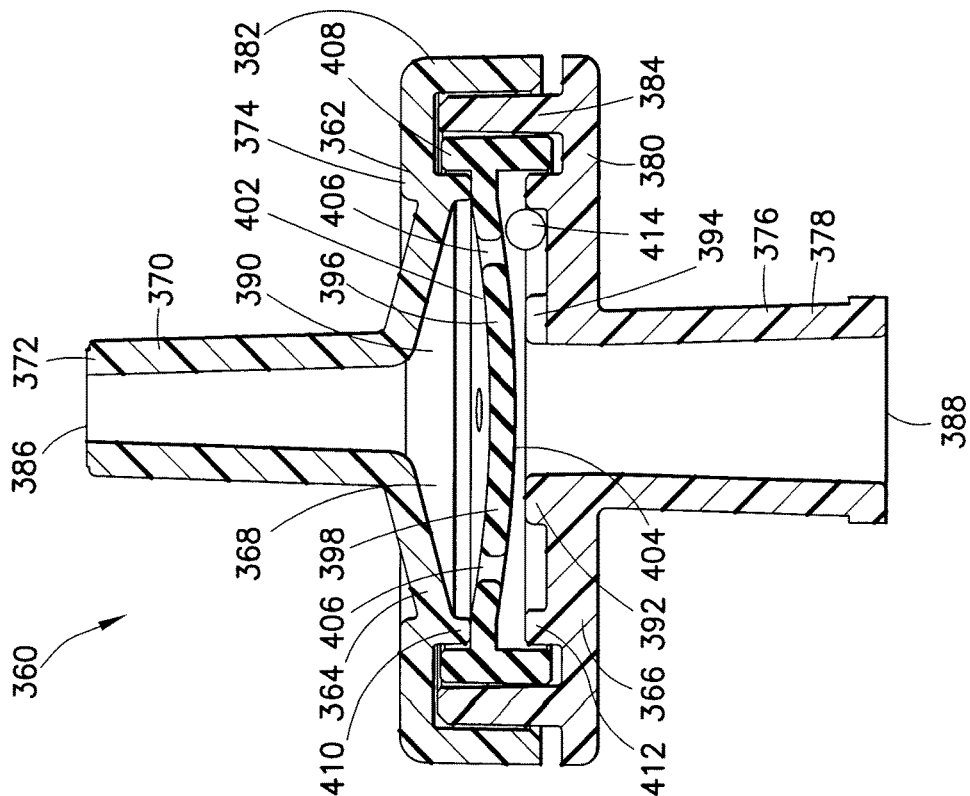
FIG. 23 is a cross-sectional view of a flow regulator showing a first position of the flow regulator according to a sixth embodiment of the present invention.
Figure 25:
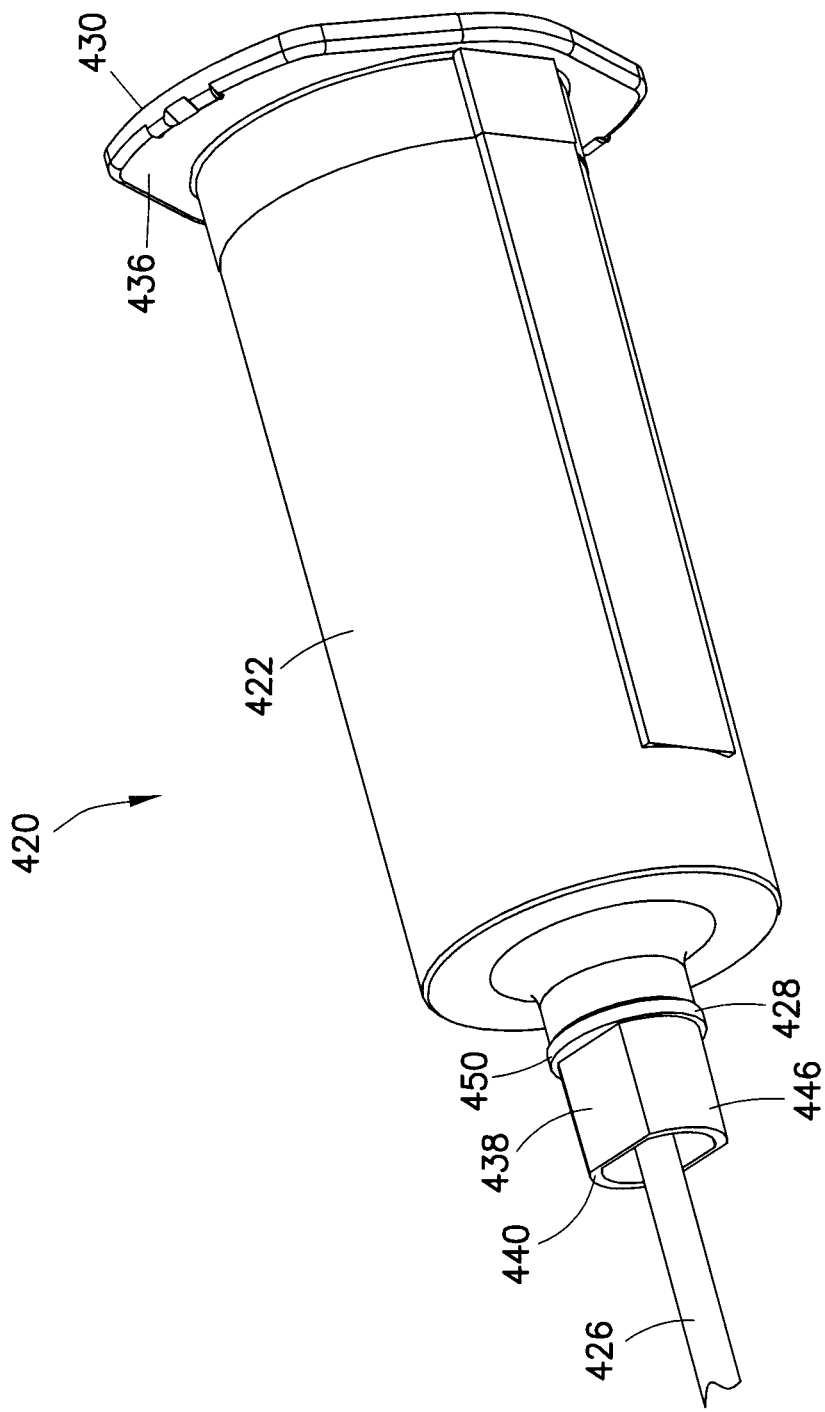
FIG. 25 is a perspective view of a blood collection set with a flow regulator according to a seventh embodiment of the present invention.
Figure 26:
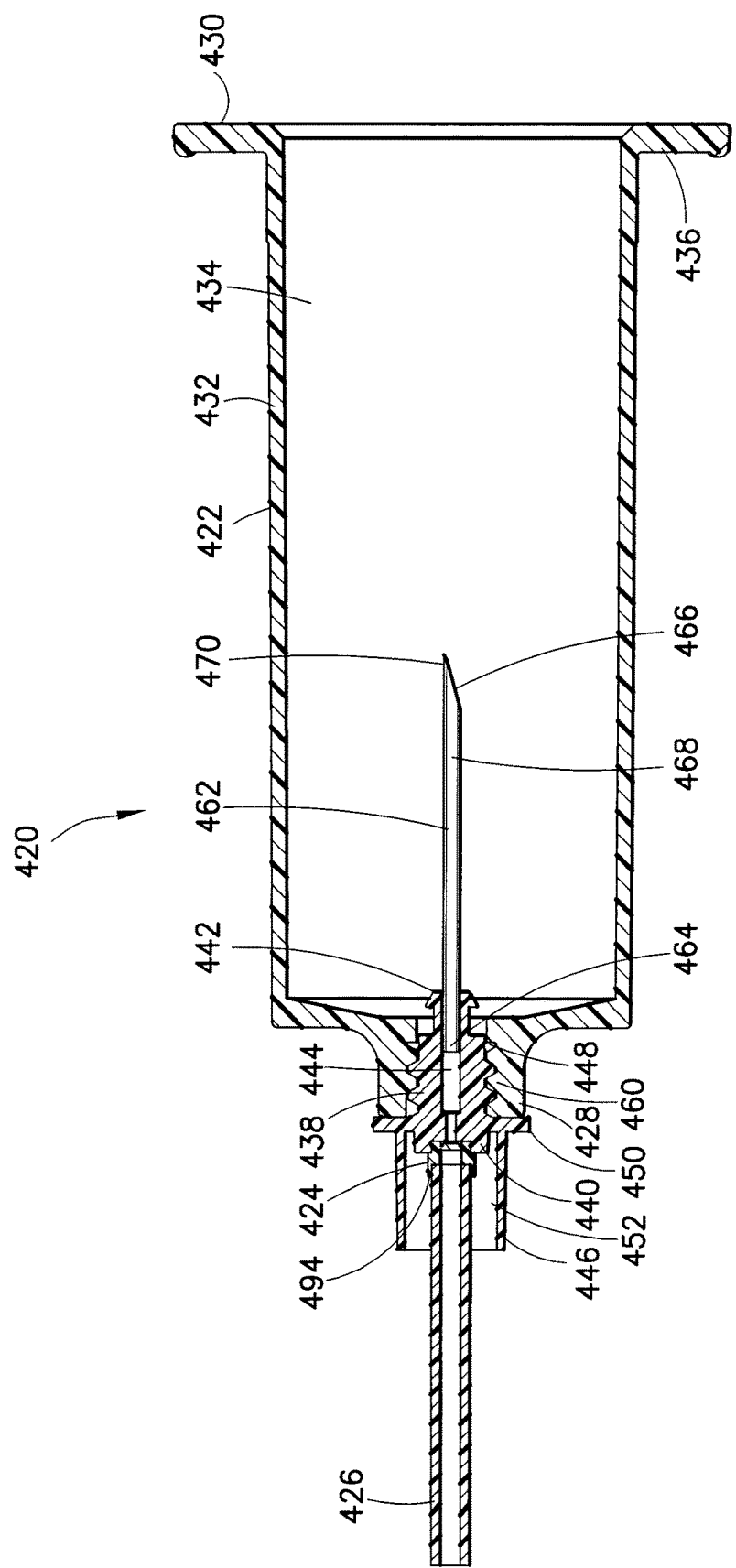
FIG. 26 is a cross-sectional view of the blood collection set of FIG. 25 in accordance with an embodiment of the present invention.
Figure 31:
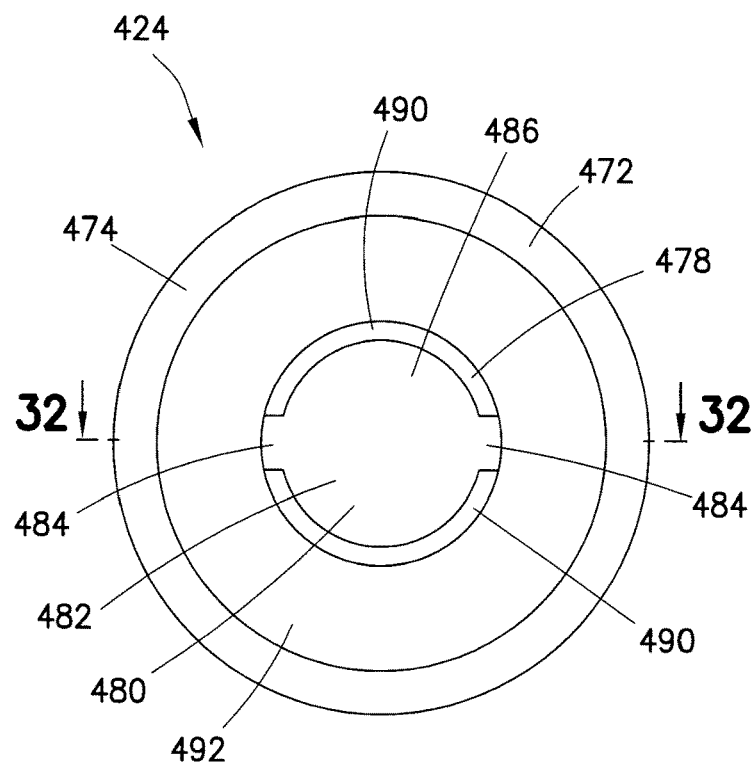
FIG. 31 is rear view of the flow regulator of FIG. 28 in accordance with an embodiment of the present invention.
Figure 32:
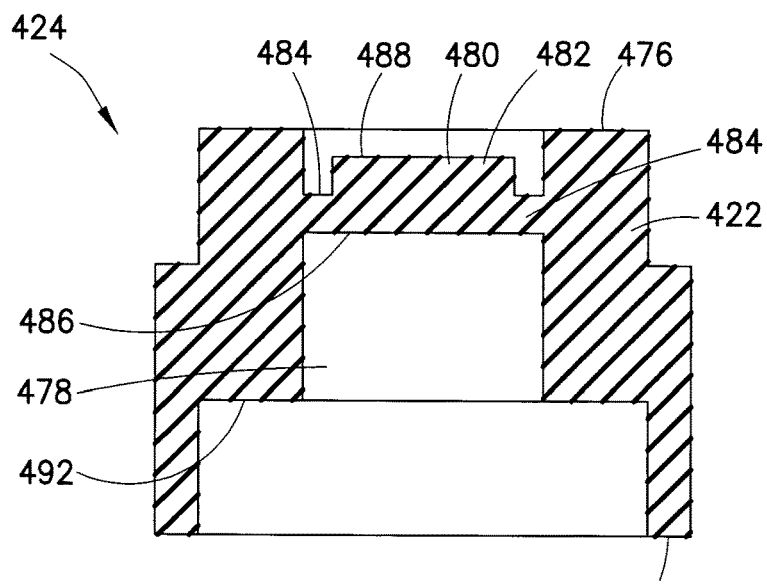
FIG. 32 is cross-sectional view of the flow regulator taken along line 32-32 in FIG. 31 in accordance with an embodiment of the present invention.

Referring to FIGS. 23 and 24, a sixth embodiment of a flow regulator 360, which is similar to the flow regulator 300 shown in FIGS. 20-22 and described above, includes a housing 362 having a first portion 364 and a second portion 366 with the first portion 364 secured to the second portion 366 to define an interior space 368. The first portion 364 of the flow regulator 360 includes a body 370 having a male luer fitting 372 and a flange 374 extending radially outward from the body 370 of the first portion 364. The second portion 366 of the flow regulator 360 includes a body 376 having a female luer fitting 378 and a flange 380 extending radially outward from the body 376 of the second portion 366. Although the first and second portions 364, 366 of the flow regulator 360 include male and female luer fittings 372, 378, the first and second portions 364, 366 may include other suitable securing arrangements conventionally utilized in connection with blood collection sets. The first and second portions 364, 366 of the flow regulator 360 each include an annular ring 382, 384 extending from the respective flanges 374, 380. The annular rings 382, 384 of the first and second portions 364, 366 are configured to engage each other via a friction or interference fit to secure the first portion 364 to the second portion 366, although other suitable arrangements for securing the first portion 364 to the second portion 366 may be utilized. The first portion 364 of the flow regulator 360 includes an inlet 386 and the second portion 366 of the flow regulator 360 includes an outlet 388 with a flow passageway 390 extending through the flow regulator 360 between the inlet 386 and the outlet 388. The second portion 366 of the housing 362 includes a generally annular membrane seat 392 positioned within the interior space 368 of the housing 362. The membrane seat 392 defines a channel 394 in fluid communication with the outlet 388, which is discussed in additional detail below.

Referring again to FIGS. 23 and 24, the flow regulator 360 further includes a membrane 396 positioned within the interior space 368 and aligned with the flow passageway 390 of the flow regulator 360. The membrane 396 has a body 398 with a concave surface 402 and a convex surface 404 positioned opposite the concave surface 402. The concave surface 402 faces the inlet 386 of the housing 362 and the convex surface 404 faces the outlet 388 of the housing 362. The body 398 of the membrane 396 defines a plurality of openings 406 extending through the body 398 from the concave surface 402 to the convex surface 404. The membrane 396 includes an annular flange 408 at a circumferential edge of the membrane 396. A perimeter of the membrane 396 is secured to the first and second portions 364, 366 of the housing 362 via annular securing projections 410, 412 provided on each of the first and second portions 364, 366 of the housing 362, which engage a portion of the membrane 396 radially inward from the flange 408 of the membrane 396. The flange 408 of membrane 396 is positioned between the annular rings 382, 384 and the annular securing projections 410, 412 of the first and second portions 364, 366 of the housing 362 such that membrane 396 is securely positioned within the interior space 368 and aligned with the flow passageway 390 of the flow regulator 360. The membrane 396 is formed from an elastomeric material and is configured to deflect in response to a difference in pressure acting on the concave and convex surfaces 402, 404 of the membrane 396 as will be discussed in more detail below. The flow regulator 360 further includes a projection 414 positioned within the interior space 368 adjacent to the second portion 366 of the housing 362. The projection 414 is a spherical shaped body, although other suitably shaped projections may be utilized.

The membrane 396 of the flow regulator 360 has a first position (shown in FIG. 23) where the flow passageway 390 between the inlet 386 and the outlet 388 of the flow regulator 360 is substantially open, and a second position (shown in FIG. 24) where the flow passageway 390 between the inlet 386 and outlet 388 is at least partially restricted. The projection 414 engages the housing 362 and the membrane 396 when the membrane 396 is in the first and second positions and lifts an outer perimeter portion of the membrane 396. When the membrane 396 is in the first position, the lift provided by the protrusion 414 is sufficient to remove the membrane 396 from the membrane seat 392 to provide a substantially open flow passageway 390. When the membrane 396 is in the second position, the membrane 396 is deflected towards the outlet 388 and engages the membrane seat 392 such that fluid flow from the inlet 386 must travel through the openings 406 in the membrane 396 and through the channel 394 of the membrane seat 392 to the outlet 388. The membrane 396 is configured to move between the first position and the second position in response to a pressure differential acting on the concave surface 402 and the convex surface 404 of the body 398 of the membrane 396. The inlet 386 of the flow regulator 360 may be secured to a wing set or needle assembly (not shown) and the outlet 388 of the flow regulator 360 may be secured to a needle holder (not shown) as discussed above in connection with FIGS. 1-11.

Referring to FIGS. 25-35, another embodiment of a blood collection set 420 includes a needle holder 422, a flow regulator 424, and a connector tube 426. The needle holder 422 has a first or distal end 428 and a second or proximal end 430 and includes a generally cylindrical-shaped sidewall 432 extending between the first and second ends 428, 430. The sidewall 432 may be formed from a transparent or translucent plastic material and defines an interior space 434 between the first and second ends 428, 430. The needle holder 422 has a flange 436 extending radially outward from the sidewall 432 at a position adjacent to the second end 430. The needle holder 422 further includes an adapter 438 secured to the first end 428 of the needle holder 422. The adapter 438 includes a first or distal end 440 and a second or proximal end 442 with a passageway 444 extending longitudinally between the first and second ends 440, 442. The adapter 438 has a receiving portion 446 positioned adjacent to the first end 440, a threaded portion 448 positioned adjacent to the second end 442, and a flange 450 extending radially outward and positioned between the receiving portion 446 and the threaded portion 448. The receiving portion 446 of the adapter 438 defines an interior space 452 and includes a recessed portion 454 having a membrane seat 456. The recessed portion 454 and membrane seat 456 define a channel 458 in fluid communication with the flow passageway 444 of the adapter 438. The threaded portion 448 of the adapter 438 is configured to engage a corresponding threaded portion 460 of the first end 428 of the needle holder 422. The second end 442 of the adapter 438 receives a cannula 462 with a first or distal end 464, a second or proximal end 466, and a lumen 468 extending between the ends 464, 466. The cannula 462 includes a proximal tip 470 that is configured to pierce an evacuated tube.

Referring to FIGS. 28-32, the flow regulator 424 includes a valve body 472 having a first end 474 and a second end 476 and defining a passageway 478 extending from the first end 474 to the second end 476. The first and second ends 474, 476 of the valve body 472 form an inlet and outlet, respectively. The flow regulator 424 further includes a membrane 480 having a body 482 and a plurality of flexible tabs 484 extending radially outward from the body 482. The membrane 480 is positioned within the passageway 478 of the valve body 472 with the plurality of flexible tabs 484 securing the membrane 480 to the valve body 472. The body 482 of the membrane 480 has a first surface 486 and a second surface 488. The membrane 480 and the valve body 472 define a plurality of openings 490 between the plurality of flexible tabs 484. The valve body 472 and membrane 480 are positioned within the interior space 452 of the adapter 438, which acts as a housing for the flow regulator 424. The second end 476 of the valve body 472 is received by the recessed portion 454 of the adapter 438 and secures the valve body 472 to the adapter 438 via an interference or friction fit, although other suitable arrangements for securing the valve body 472 to the adapter 438 may be utilized. The first end 474 of the valve body 472 defines a recessed portion 492 that is configured to receive an end 494 of the connector tube 426. The membrane 480 and the plurality of flexible tabs 484 are formed from an elastomeric material and are configured to deflect in response to a difference in pressure acting on the first and second surfaces 486, 488 of the membrane 480 as will be discussed in more detail below.

Referring to FIGS. 25-30, the blood collection set 420 is assembled by securing the second end 476 of the valve body 472 to the recessed portion 454 of the adapter 438 of the needle holder 422. The end 494 of the connector tube 426 is secured to the first end 474 of the valve body 472 via an interference or friction fit, although other suitable arrangements for securing the connector tube 426 to the valve body 472 may be utilized. The other end (not shown) of the connector tube 426 is secured to a wing set (not shown), which is configured to pierce a targeted blood vessel of a patient. Although the adapter 438 of the needle holder 422 acts as a housing for the flow regulator 424, a wing set or needle assembly (not shown) may also form a housing for receiving the valve body 472 and membrane 480. In use, a phlebotomist guides the wing set or needle assembly of the blood collection set into a targeted blood vessel. After access to the blood vessel has been attained, the phlebotomist inserts an evacuated tube (not shown) into the needle holder 422 with fluid flowing from the wing set or needle assembly through the flow regulator 424, through the cannula 462 of the needle holder 422, and into the evacuated tube. More specifically, fluid flows through the connector tube 426, into the valve body 472, through the plurality of openings 490 defined by the membrane 480 and valve body 472, through the passageway 444 of the adapter 438, and into the lumen 468 of the cannula 462.

Figure 33:
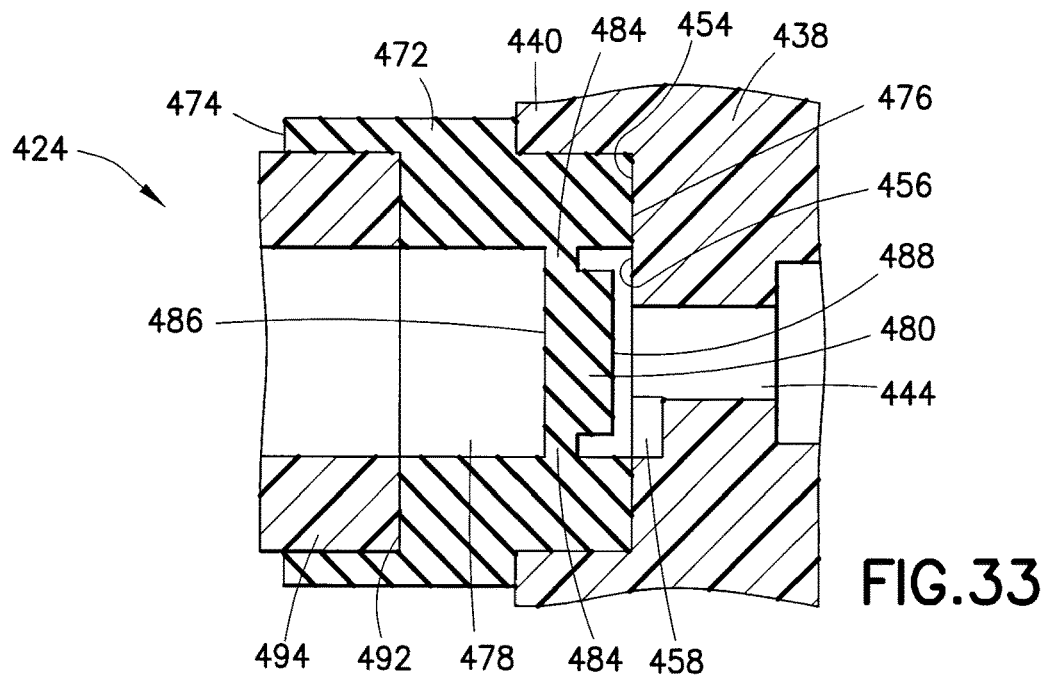
FIG. 33 a partial cross-sectional view of the blood collection set of FIG. 25 showing a first position of the flow regulator in accordance with an embodiment of the present invention.
Figure 34:
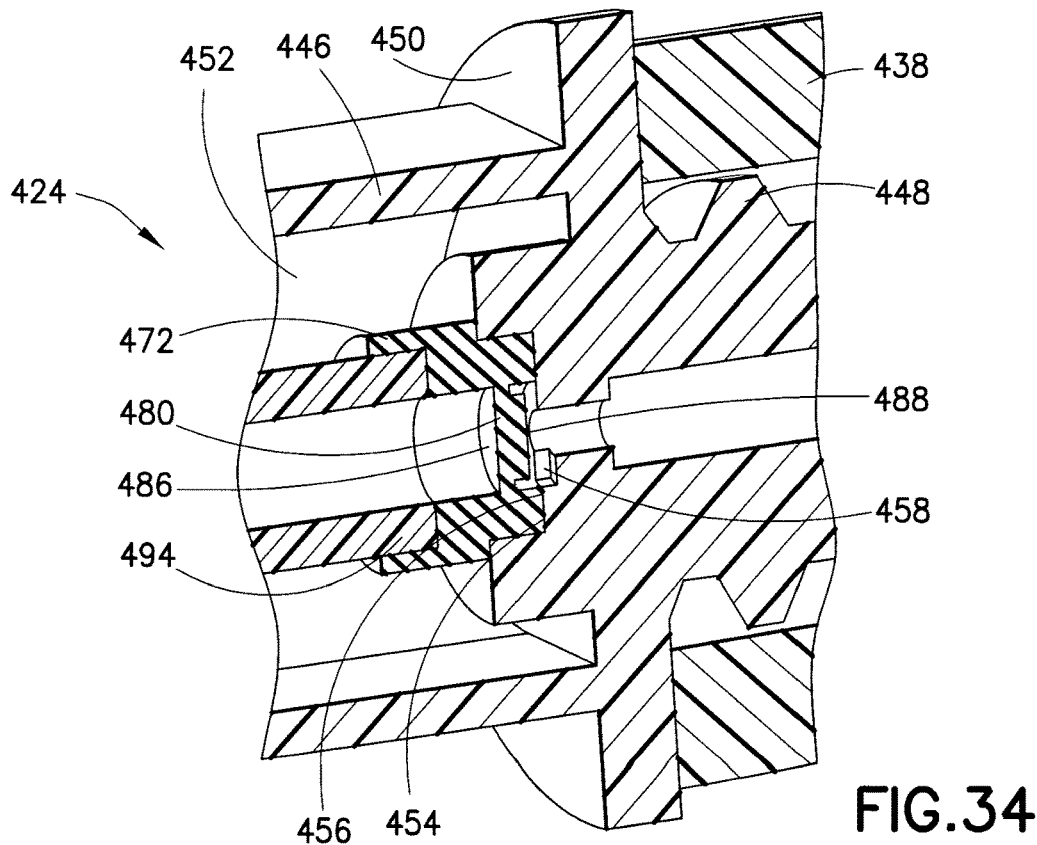
FIG. 34 is a partial perspective cross-sectional view of the blood collection set of FIG. 25 showing a first position of the flow regulator in accordance with an embodiment of the present invention.
Figure 35:
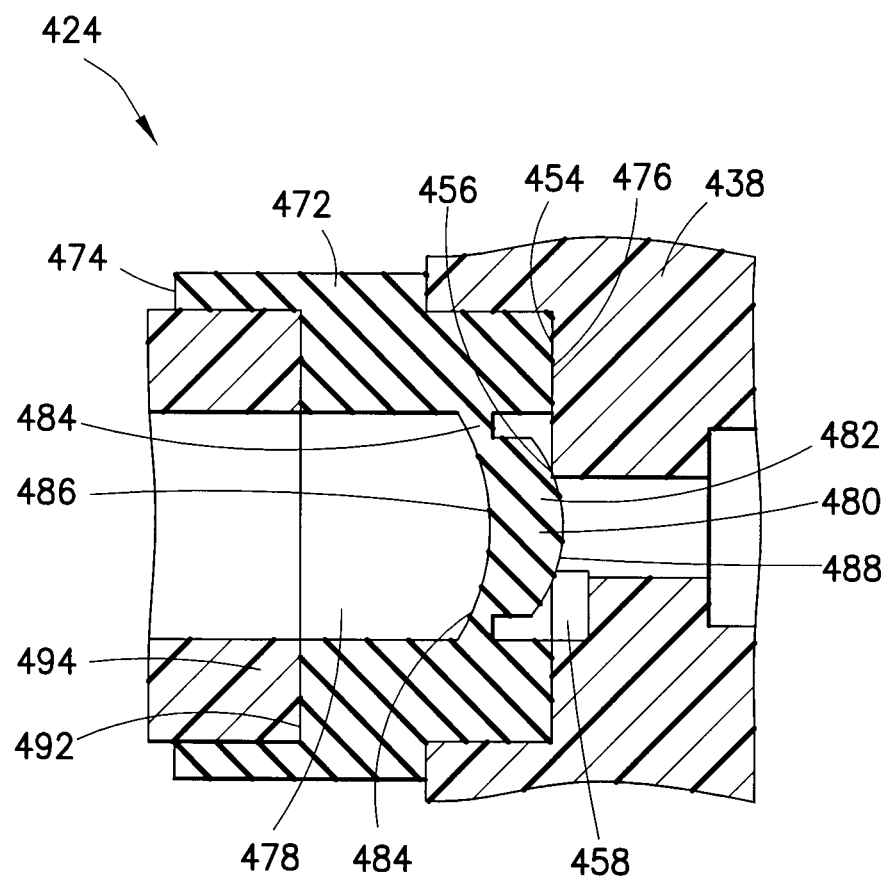
FIG. 35 is a partial cross-sectional view of the blood collection set of FIG. 25 showing a second position of the flow regulator in accordance with an embodiment of the present invention.

Referring to FIGS. 33-35, the membrane 480 of the flow regulator 424 has a first position (shown in FIGS. 33 and 34) where the flow passageway 478 between the inlet and the outlet of the flow regulator 424 is substantially open, and a second position (shown in FIG. 35) where the membrane 480 is deflected to at least partially restrict the flow passageway 478. The flow regulator 424 operates in a similar manner as the flow regulator 14 shown in FIGS. 1-11 and described above. In particular, when the membrane 480 is in the second position, the membrane 480 and the flexible tabs 484 are deflected such that the membrane 480 engages the membrane seat 456 at the recessed portion 454 of the adapter 438. In the second position, fluid flow from the connector tube 426 must travel through the plurality of openings 490 and through the channel 458 of the recessed portion 454 of the adapter 438 to reach the cannula 462. Accordingly, when the membrane 480 is in the second position, the flow of fluid from the connector tube 426 to the cannula 462 must pass through the channel 458 which partially restricts the flow from the connector tube 426 to the cannula 462. The membrane 480 is configured to move between the first position and the second position in response to a pressure differential acting on the first and second surfaces 486, 488 of the membrane 480.

Figure 36:
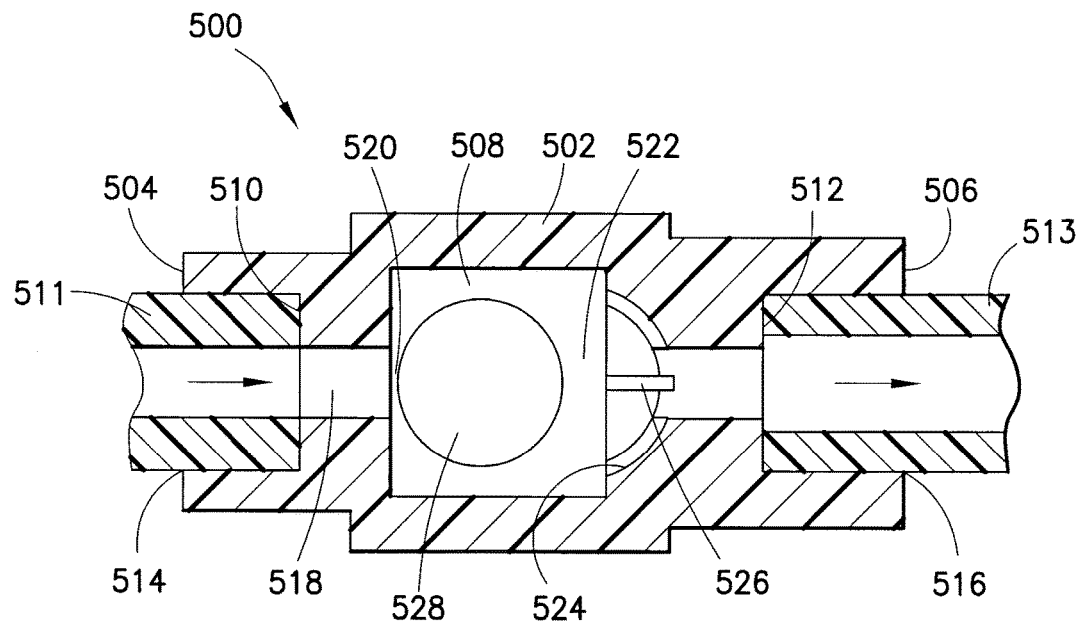
FIG. 36 is a cross-sectional view of a flow regulator showing a first position of the flow regulator according to an eighth embodiment of the present invention.
Figure 37:
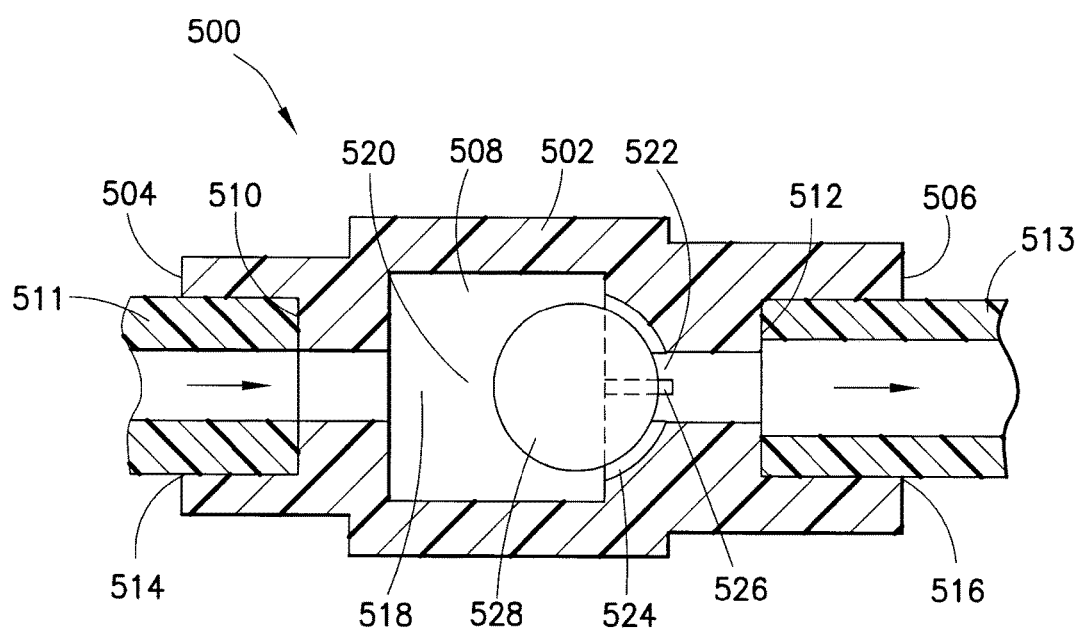
FIG. 37 is a cross-sectional view of the flow regulator of FIG. 36 showing a second position of the flow regulator in accordance with an embodiment of the present invention.

Referring to FIGS. 36 and 37, an eighth embodiment of a flow regulator 500 includes a housing 502 having a first end 504 and a second end 506 and defines an interior space 508 between the first and second ends 504, 506. The first and second ends 504, 506 of the flow regulator 500 each include a recessed portion 510, 512 configured to receive respective ends of first and second tubes 511, 513. The first end 504 of the flow regulator 500 includes an inlet 514 and the second end 506 of the flow regulator 500 includes an outlet 516 with a flow passageway 518 extending through the flow regulator 500 between the inlet 514 and the outlet 516. The interior space 508 has an inlet side 520 and an outlet side 522. The housing 502 also includes a valve seat 524 positioned within the interior space 508 with the valve seat 524 defining a channel 526 in fluid communication with the outlet 516. The flow regulator 500 further includes a valve member 528 positioned within the interior space 508. The valve member is a spherical body, although other suitably shaped valve members may be utilized.

Referring again to FIGS. 36 and 37, the valve member 528 of the flow regulator 500 has a first position (shown in FIG. 36) where the flow passageway 518 between the inlet 514 and the outlet 516 of the flow regulator 500 is substantially open, and a second position (shown in FIG. 37) where the flow passageway 518 between the inlet 514 and outlet 516 is partially restricted. When the valve member 528 is in the second position, the valve member 528 engages the valve seat 524 such that fluid flow from the inlet 514 must travel through the channel 526 of the valve seat 524 to the outlet 516. Accordingly, when the valve member 528 is in the second position, the flow of fluid from the inlet 514 to the outlet 516 must pass through the channel 526 which partially restricts the flow between the inlet 514 and outlet 516. The valve member 528 is configured to move between the first position and the second position in response to a pressure differential acting on the inlet side 520 of the valve member 528 and the outlet side 522 of the valve member 528. Although the flow regulator 500 is shown connected in-line with first and second tubes 511, 513, the flow regulator 500 may be directly secured to a wing set or needle assembly (not shown).

Figure 38:
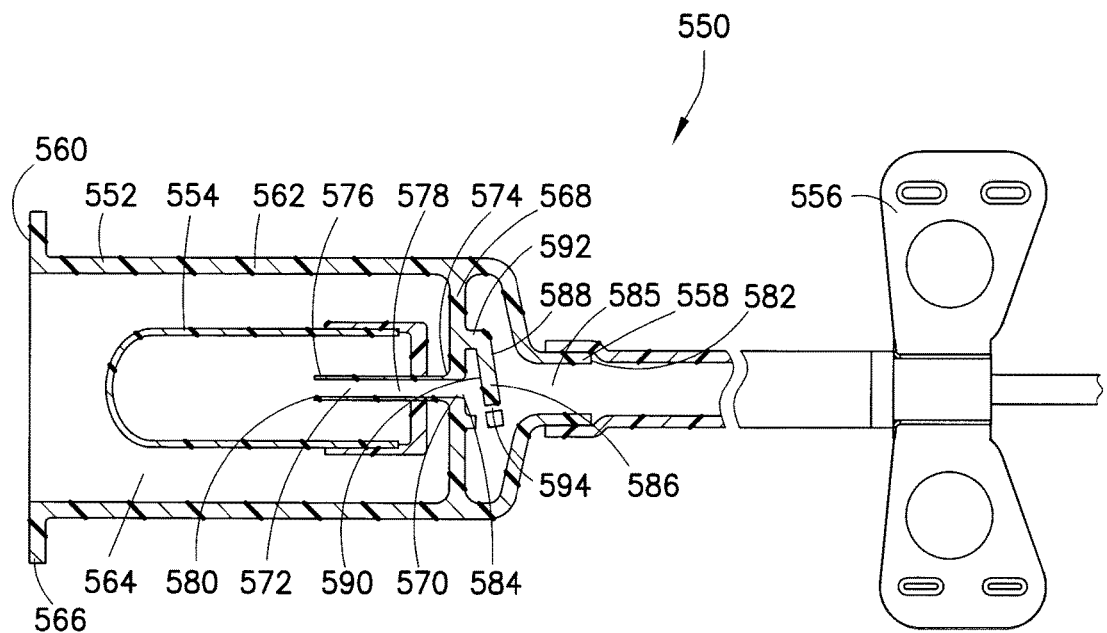
FIG. 38 is a cross-sectional view of a portion of a blood collection set with a flow regulator according to a ninth embodiment of the present invention.
Figure 38A:
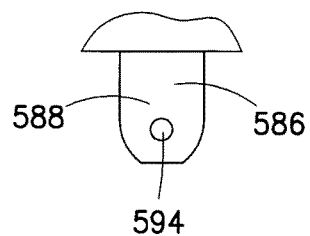
FIG. 38A is a front view of a valve member utilized in the flow regulator of FIG. 38 in accordance with an embodiment of the present invention.
Figure 39:
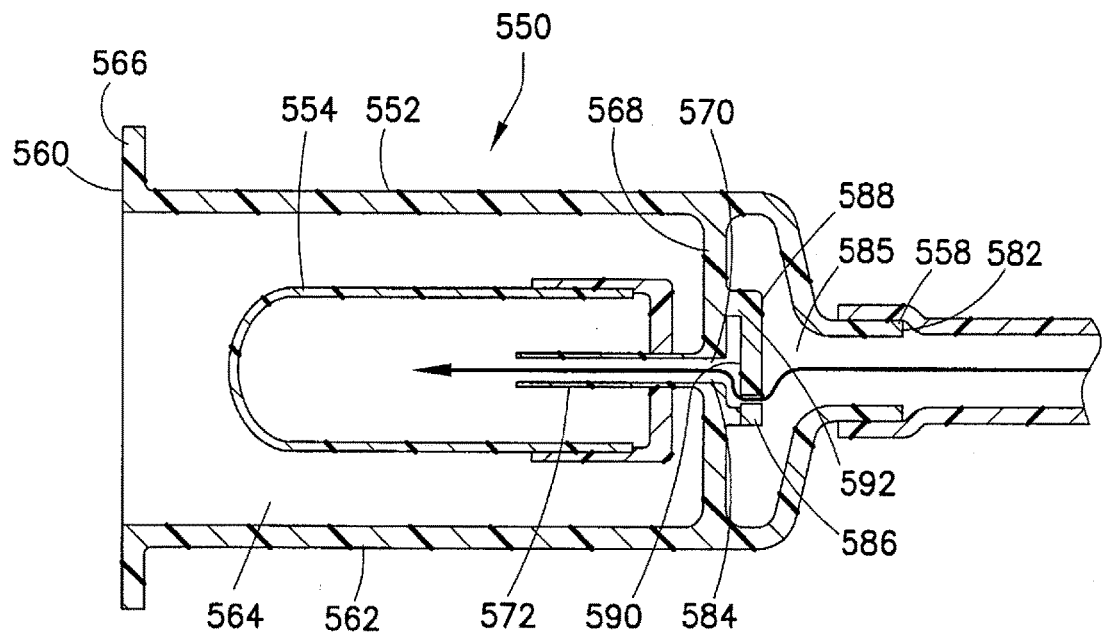
FIG. 39 is a cross-sectional view of the flow regulator of FIG. 38 showing a first position of the flow regulator in accordance with an embodiment of the present invention.
Figure 40:
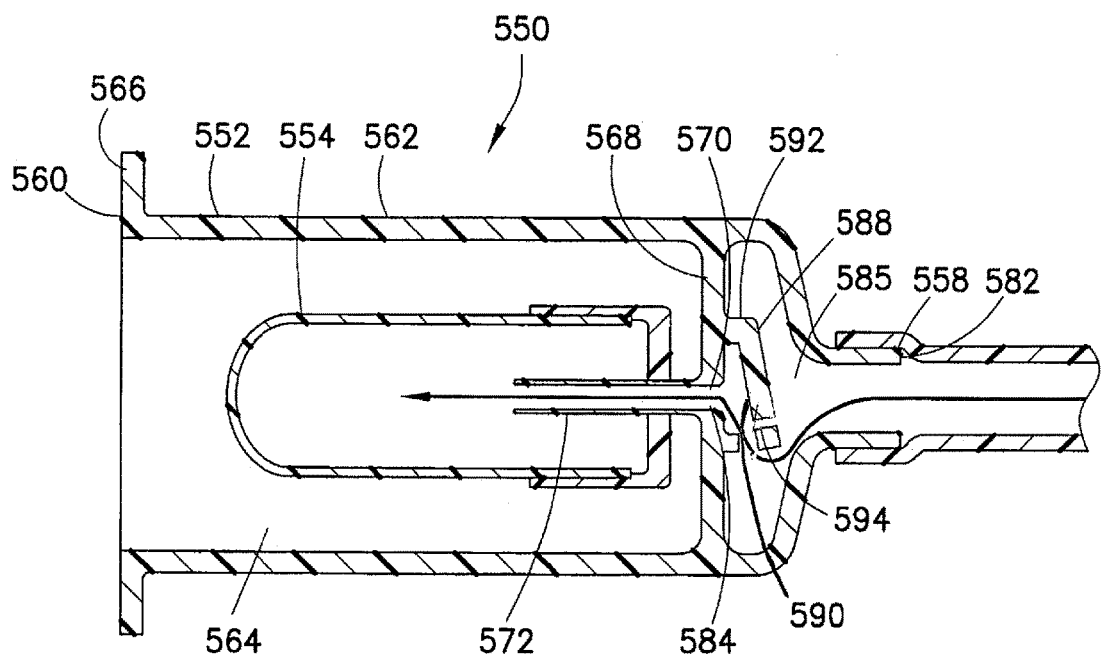
FIG. 40 is a cross-sectional view of the flow regulator of FIG. 38 showing a second position of the flow regulator in accordance with an embodiment of the present invention.

Referring to FIGS. 38-40, a further embodiment of a flow regulator 500 includes a needle holder 552, an evacuated tube 554, and wing set 556. The needle holder 552 has a first or distal end 558 and a second or proximal end 560 and includes a generally cylindrical-shaped sidewall 562 extending between the first and second ends 558, 560. The sidewall 562 may be formed from a transparent or translucent plastic material and defines an interior space 564 between the first and second ends 558, 560. The needle holder 552 has a flange 566 extending radially outward from the sidewall 562 at a position adjacent to the second end 560. An interior wall 568 extends transversely between opposite sides of the sidewall 562 within the interior space 564 and defines an opening 570 for receiving a cannula 572. The cannula 572 has a first or distal end 574, a second or proximal end 576, and a lumen 578 extending between the ends 574, 576. The cannula 572 includes a proximal tip 580 that is configured to pierce an evacuated tube. The first end 558 of the needle holder 552 forms an inlet 582 and the opening 570 of the interior wall 568 forms an outlet 584 with a flow passageway 585 extending therebetween. A valve member 586 having a first surface 588 and a second surface 590 is positioned within the interior space 564 and is secured to the interior wall 568 via a flexible hinge 592. As shown more clearly in FIG. 38A, the valve member 586 is an elongate shaped member and defines an opening 594. A wing set 556 is secured to the first end 558 of the needle holder 552. The blood collection set 550 is assembled and used in a similar manner as the blood collection set 10 shown in FIGS. 1-11 and described above.

Referring to FIGS. 39-40, the valve member 586 has first position (shown in FIG. 40) where the flow passageway 585 between the inlet 582 and the outlet 584 is substantially open, and a second position (shown in FIG. 39) where the valve member 586 is at least partially disposed over the outlet 584 to at least partially restrict the flow passageway 585 between the inlet 582 and the outlet 584. In the second position, the valve member 586 is biased to cover the opening 570 in the interior wall 568 with the flow of fluid only passing through the opening 594 in the valve member 586, which restricts the flow and reduces the flow rate from the wing set 556 to the evacuated tube 554. The valve member 586 is configured to move between the first position and the second position in response to a pressure differential acting on the first and second surfaces 588, 590 of the valve member 586.

While several embodiments of a fluid sample collection device and method were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A flow regulator for a blood collection assembly comprising:
 a housing having an inlet and an outlet and defining an interior space between the inlet and the outlet; and
 an elongate shaped membrane having a first surface and a second surface disposed at least partially within the interior space, the elongate shaped membrane secured to the housing via a flexible member at a first side, wherein a second side of the elongate shaped membrane opposite the first side is unattached to the housing, the elongate shaped membrane having a first position wherein a flow path between the inlet and the outlet is substantially open, and a second position wherein the flow path between the inlet and the outlet is partially restricted, the elongate shaped membrane configured to move between the first and second positions in response to a pressure differential acting on the elongate shaped membrane, wherein the elongate shaped membrane has at least one opening defined therein in fluid communication with the inlet and the outlet in each of the first position and the second position of the elongate shaped valve member, wherein the at least one opening is defined between the first and second ends of the elongate shaped membrane, wherein the flow of fluid passes through only the at least one opening of the elongate shaped membrane when the elongate shaped membrane is in the second position, and wherein a portion of the elongate shaped membrane not including the at least one opening is biased to cover an entirety of another opening forming the outlet in the second position.

2. A flow regulator for a blood collection assembly comprising:
  a housing having an inlet and an outlet and defining an interior space between the inlet and the outlet, the interior space having an inlet side and an outlet side; and
  a valve positioned within the interior space, the valve having a base secured to the housing and an elongate shaped valve member secured to the base via a flexible member at a first side, wherein a second side of the elongate shaped valve member opposite the first side is unattached to the housing, the elongate shaped valve member having a first position wherein a flow path between the inlet and the outlet is substantially open, and a second position wherein the flow path between the inlet and the outlet is partially restricted, the elongate shaped valve member configured to move between the first and second positions based on a pressure differential acting on an inlet side of the elongate shaped valve member and an outlet side of the elongate shaped valve member, wherein the valve member has at least one opening defined therein in fluid communication with the inlet and the outlet in each of the first position and the second position of the elongate shaped valve member, wherein the at least one opening is defined between the first and second ends of the elongate shaped valve member, wherein the flow of fluid passes through only the at least one opening of the elongate shaped valve member when the elongate shaped valve member is in the second position, and wherein, in the second position, the at least one opening is in fluid communication with another opening forming the outlet and completely coaxially offset from the another opening forming the outlet.

3. A flow regulator for a blood collection assembly comprising:
  a housing having an inlet and an outlet and defining an interior space between the inlet and the outlet, the housing having a valve seat; and
  an elongate shaped valve member having a first surface and a second surface, the valve member positioned within the interior space and secured to the housing via a flexible hinge at a first side, wherein a second side of the elongate shaped valve member opposite the first side is unattached to the housing, the elongate shaped valve member having a first position wherein a flow path between the inlet and the outlet is substantially open, and a second position wherein the elongate shaped valve member is disposed over the outlet to partially restrict the flow path between the inlet and the outlet, wherein the elongate shaped valve member is configured to move between the first and second positions based on a pressure differential acting on the first surface of the elongate shaped valve member and the second surface of the elongate shaped valve member, wherein the valve member has at least one opening defined therein in fluid communication with the inlet and the outlet in each of the first position and the second position of the elongate shaped valve member, wherein the at least one opening is defined between the first and second ends of the elongate shaped valve member, wherein the flow of fluid passes through only the at least one opening of the elongate shaped valve member when the elongate shaped valve member is in the second position, and wherein a portion of the elongate shaped valve member not including the at least one opening is biased to cover an entirety of another opening forming the outlet such that, in the second position, the at least one opening is in fluid communication with the another opening forming the outlet and completely coaxially offset from the another opening forming the outlet.

4. The flow regulator of claim 3, wherein the housing comprises a needle holder configured to receive an evacuated container.

5. The flow regulator of claim 4, wherein the needle holder includes a cannula having a proximal end and a distal end, and wherein the valve member is aligned with the distal end of the cannula.

* * * * *